(12) United States Patent
Bonde et al.

(10) Patent No.: US 6,699,709 B1
(45) Date of Patent: Mar. 2, 2004

(54) METHOD FOR DETERMINATION OF THE GROSS NITROGEN-MINERALIZATION RATE OF A SOIL SAMPLE

(75) Inventors: Torben A. Bonde, Lange-Mullers Allé 27 Sophienberg Vaenge 17, DK-2960 Rungsted Kyst (DK); Morten Miller, Mathildevej 7, II th., DK-2000 Frederiksberg (DK); Jan Sørensen, Søborg (DK)

(73) Assignees: Torben A. Bonde, Rungsted Kyst (DK); Morten Miller, Frederiksberg (DK)

( * ) Notice: Subject to any disclaimer, the term of this patent is extended or adjusted under 35 U.S.C. 154(b) by 0 days.

(21) Appl. No.: 09/581,319

(22) PCT Filed: Dec. 10, 1998

(86) PCT No.: PCT/IB98/01984
§ 371 (c)(1),
(2), (4) Date: Aug. 21, 2000

(87) PCT Pub. No.: WO99/29893
PCT Pub. Date: Jun. 17, 1999

(30) Foreign Application Priority Data

Dec. 10, 1997 (DK) ............................................ 1436/97

(51) Int. Cl.[7] ................................................ B09B 3/00
(52) U.S. Cl. ........................................ 435/262.5; 71/1
(58) Field of Search .............................. 435/262.5, 975; 71/1, 6, 28, 30

(56) References Cited

PUBLICATIONS

Appel, T., "Relevance of soil nitrogen mineralization, total nitrogen demand of crops, and efficiency of applied nitrogen for fertilizer recommendations for cereals." Zeitschrift fur Pflanzenernahrung und Bodenkunde, vol. 157(6), pp. 407–414, 1994.*
Abstract of SU–657–344.
Abstract of SU–711–470.
Galstyan, et al., "Determination of the Arginase Activity of the Soil," Chemical Abstracts 92:494 (1980).
Cole, "Controlling Environmental Nitrogen Through Microbial Metabolism," TIBTECH 11:368–372 (1993).
Abstract of Benchemsi–Bekkari, et al., "Black Locust Nitrogen Nutrition. Urea Metabolism, Relation with Arginase and Urease Activiteis," Pascal No. 94–0041061.
Alef, et al., "A Comparison of Methods to Estimate Microbial Biomass and N–Mineralization in Agricultural and Grassland Soils," Soil Biol. Biochem. 20(4):561–565 (1988).
Alef, et al., "Arginine Ammonification, A Simple Method to Estimate Microbial Activity Potentials in Soils," Soil Biol. Biochem 18(2):233–235 (1986).
Pedersen, et al., "Evidence for Bacterial Urea Production in Marine Sediments," FEMS Microbiology Ecology 12:51–59 (1993).
Neilsen, et al., "Significance of Microbial Urea Turnover in N cycling of Three Danish Agricultural Soils," FEMS Microbiology Ecology pp. 1–11 (1997).
Burton, et al., "Spatial and Temporal Fluctuation in Biomass, Nitrogen Mineralizing Reactions and Mineral Nitrogen in a Soil Cropped to Barley," Can. J. Soil Sci. 72:31–42 (1992).
Galstyan, et al., "Determination of the Arginase Activity of the Soil," Dokladiy Akademii Nauk Armyanskoi SSR 69(2):125–128 (1979).
Araksyan, et al., "Effect of Nitrogen Fertilizers on the Activity of Nitrogen Metabolism Enzymes and Soil Nitrogen Form," Biologicheskii Zhurnal Armenii 41(11):946–949 (1988).
Kandeler, et al., "Microbioal Biomass, N Mineralization, and the Activities of Various Enzymes in Relation to Nitrate Leaching and Root Distribution in a Slurry–amended Grassland," Biol. Fertil. Soils 18:7–12 (1994).
Rowell, et al., "Characteristics Associated with Differences Between Undisturbed and Industrially–Disturbed Soils," Soil Biol. Biochem. 25(11):1499–1511 (1993).
Oliver, et al., "The Arginine Ammonification: Determination of Microbial Activity of the Nitrogen Status of Soils?".

* cited by examiner

Primary Examiner—Ralph Gitomer
(74) Attorney, Agent, or Firm—Iver P. Cooper

(57) ABSTRACT

The invention facilitates a determination of the rate at which soil organic nitrogen is converted to inorganic nitrogen or mineral nitrogen. This conversion is known as N-mineralization. The total release of plant available nitrogen in a soil, i.e., the gross N-mineralization rate quantifies the conversion in the soil of organic nitrogen to inorganic nitrogen. The present invention provides a quick and reliable method for measuring the gross N-mineralization rate of a soil sample. The method exploits that a microbial enzyme activity of a functional ornithine acid cycle present in said sample is correlatale with the rate or gross N-mineralization of that same sample. The method of the invention can be used e.g. in a determination of the amount of a nitrogen-containing fertilizer to be applied to a soil such as e.g. a field of agricultural crops.

64 Claims, 15 Drawing Sheets

METHOD FOR DETERMINATION OF THE GROSS NITROGEN-MINERALIZATION RATE OF A SOIL SAMPLE

TECHNICAL FIELD

The present invention relates to a method for determination of the gross nitrogen-mineralization rate of a soil sample. There is also provided a method for determining the amount of fertiliser to be applied to a soil and a test kit for readily determining a soil microbial enzyme activity present in a soil sample and correlating this activity with the corresponding gross nitrogen-mineralization rate of said sample.

More particularly, the invention provides for a novel and innovative method for determining the total release of plant available nitrogen (N) in soils. Soils contain nitrogen in both organic and inorganic forms. Both forms are potentially available for uptake by agricultural crops. However, organic forms must be converted to inorganic nitrogen before plant uptake.

The invention facilitates a determination of the rate at which organic nitrogen is converted to inorganic nitrogen or mineral nitrogen. This conversion is known as N-mineralization. The total release of plant available nitrogen in a soil, i.e. the gross N-mineralization rate quantifies the conversion in the soil of organic nitrogen to inorganic nitrogen.

The method of the invention can be used e.g. in a determination of the amount of a nitrogen-containing fertiliser to be applied to a soil such as e.g. a field of agricultural crops. Determination of the total release of plant available nitrogen in an agricultural soil is important when considering how much nitrogen-fertiliser to apply in order to obtain optimal growth conditions and at the same time minimising inorganic nitrogen-compounds such as nitrate from leaching out of the soil into ground or surface waters.

BACKGROUND OF THE INVENTION

Nitrogen is present in the soil in both organic and inorganic forms. Nitrogen present in what is generally referred to as "soil organic matter" (SOM) such as macromolecular proteinaceous substances, humus, lignine, pectine, and the like, cannot readily be taken up be growing plants including agricultural crops. Nitrogen must be present in inorganic forms such as e.g. nitrate, ammonia in order to be taken up via the roots of the crops. The amount of inorganic nitrogen in the soil is generally much less than the requirement of the crops for nitrogen. It is therefore necessary to supplement nitrogen in the form of a suitable fertiliser.

An optimal fertiliser application shall facilitate optimal plant growth as well as minimal nitrogen leaching. Determination of the total release of plant available nitrogen in a soil is thus essential, when considering just how much nitrogen-fertiliser to apply, in order to achieve optimal growth conditions as well as preventing inorganic nitrogen-compounds such as nitrate from leaching out of the soil. Without any knowledge of the soils inherent capacity to release nitrogen to the crops, the farmer cannot accurately determine the amount of nitrogen-fertiliser to apply.

The conversion of organic nitrogen to nitrogen present in inorganic forms such as nitrate and ammonia is a dynamic and complex process, which cannot easily be accounted for. The process is influenced by e.g. climate, soil texture, total nitrogen, soil management, and the presence of soil microorganisms capable of degrading organic macromolecules and releasing e.g. nitrate and/or ammonia into the soil, and by the amount of nitrogen taken up by crops.

No simple method is available for measuring the gross N-mineralization rate. Thus, it has hitherto not been possible to account for nitrogen mineralization in fertiliser planning. Various methods for measuring directly or indirectly the amount and/or presence of organic and/or inorganic nitrogen-containing compounds in soil have been described in the prior art and briefly reviewed below.

Burton and McGill (1992) reported on changes in various components of a so called N-mineralization cascade. The changes studied included those of a specific component, such as a deaminase, as well as highly integrated components, such as a biomass. The selected soil was a Black Chernozemic seeded to barly (*Hordeum vulgare L.*) under field conditions. Changes in enzyme contents were related to soil ammonium in order to determine, if the microbial environment changed sufficiently to exert feedback control on N-mineralizing reactions, which would allow them to be detected. Histidase and protease were chosen as model systems for depolymerization and deamination, respectively, because information was already available on their control in pure culture studies, on histidine content and control of histidase in soil, and because assay procedures were readily available for soils. A correlation of an enzyme activity with gross N mineralization rates of a soil and problems associated with excessive use of fertilisers were not disclosed therein.

Burton and McGill (1989) characterised the stability of L-histidine $NH_3$-lyase in soil by using a kinetic analysis and enzymatic assays in the presence of a biostatic agent. The objective was to employ a range of assay durations together with a kinetic analysis in order to examine the components of L-histidine $NH_3$-lyase activity in soil, the stability of such components and the implications for the control of this enzyme. A correlation of an enzyme activity with gross N mineralization rates of a soil and problems associated with excessive use of fertilisers were not disclosed therein.

Galstyan and Vartanyan (Chem. Abstracts (1980), vol. 92, p. 494, 92:93207k) describe a method for determining an enzyme activity, i.e. arginase activity in soil samples by titration of ammonium ions. The results demonstrate a correlation of the content of humus with microbial activities, but do not evaluate or consider evaluating a correlation of an enzyme activity with gross N-mineralization rates of a soil.

SU-657344 relates e.g. to a calorimetric determination of inorganic nitrate and nitrate reducing enzymes in soil. The method is useful in evaluating nitrogen fixing soil bacterial activities. A correlation of an enzyme activity with gross N-mineralization rates of a soil and problems associated with excessive use of fertilisers were not disclosed.

SU-711470 relates to a determination of plant available nitrogen in a soil sample in order to evaluate a potential fertiliser requirement. A correlation of an enzyme activity with gross N-mineralization rates of a soil and problems associated with excessive use of fertilisers were not disclosed. Derwent Abstract WPI 96-391776 discloses a simple incubation method for determining the net mineralization potential of a soil. No enzymes are mentioned and consequently, a correlation of an enzyme activity with gross N-mineralization rates of a soil and problems associated with excessive use of fertilisers were not disclosed.

Derwent Abstract WPI 93-248897 discloses a method for calculating the net mineralization potential of a soil. A correlation of an enzyme activity with gross N-mineralization rates of a soil and problems associated with excessive use of fertilisers were not disclosed.

Cole (TIBTECH (1993), vol. 11, p. 368–372) describes the need to control environmental nitrogen in various ecosystems by means of exploiting microbial metabolisms, but no solution to the problem of how to reduce the excessive use of fertilisers is presented.

Benchemsi-Bekkari and Pizelle (Black locust nitrogen nutrition. Urea metabolism, relation with arginase and urease activities, Ph.D. thesis, (1993), Pascal no. 94-0041061) describe an acacia tree capable of assimilating nitrogen. Metabolism relating to the urea cycle is disclosed and a ratio of arginase activity to urease activity is determined. A correlation of arginase activity with gross N-mineralization rates of a soil and problems associated with excessive use of fertilisers are not disclosed.

Biosis Acc. No. 37066711 relates to a study of the effect of nitrogen-fertilisers on soil enzymes involved in nitrogen uptake and nitrogen metabolism in soil bacteria. A correlation of an enzyme activity with gross N-mineralization rates of a soil is not disclosed.

It is desirable to be able to determine in an accurate manner the significant variations in the release of inorganic nitrogen in a soil throughout the year. The essential question is how to accurately account for the gradual mineralization of organic nitrogen? Presently, no simple and inexpensive methods are available for measuring N-mineralization in soils, and only a limited knowledge of N-mineralization and crop nitrogen-demand has so far been extracted from field experiments analysing the response of crops to various nitrogen-fertilisers.

When calculating the amount of a fertiliser to apply to an agricultural field, the farmer must consider the nitrogen-demand of the crop in question. Crop nitrogen-demand has been determined for a wide range of different crops. As an example, a wheat crop usually requires ca. 180 kg nitrogen per hectare, while a spring barley crop usually requires ca. 120 kg nitrogen per hectare.

An illustration of the need to apply nitrogen-fertilisers to agricultural soils is given below. A 10 tonnes yield in winter wheat, which is often achieved by farmers in northern Europe, will have a content of some 200 kg nitrogen in the grains, a content of 40 kg nitrogen in the straws and a further content of 30 kg nitrogen in the roots and stubble. This gives a total nitrogen requirement of 270 kg nitrogen per hectare. The winter wheat may be grown on a soil containing as much as 5000 kg organic nitrogen per ha. 1–3% of this total amount of organic nitrogen, i.e. 50–150 kg nitrogen per hectare is mineralized each year, i.e. converted to inorganic nitrogen, which can be taken up by the plants. At the high level of 150 kg nitrogen mineralized per year, the crops will still require a supplement of nitrogen of about 180 kg nitrogen per hectare each year, assuming that 30–40% of such a supplement is leached or otherwise lost.

In another illustration of the significant contribution made by the N-mineralization process to the total amount of plant available nitrogen in the soil, a field of spring barley may need 120 kg nitrogen per year per ha. The process of N-mineralization may contribute as much as 50–100 kg, and consequently, the farmer, when taking this into account, will have to add the extra 20–70 kg by means of a fertiliser. The example illustrates two important things: Firstly, the N-mineralization is a major contributor of nitrogen compared to the amount of nitrogen provided in the form of a fertiliser, and secondly, it has not previously been possible to make an accurate assessment of the rate of N-mineralization.

Although the nitrogen-fertiliser demand of a certain crop on a particular field is primarily a function of the crop itself, the resulting fertiliser demand will obviously be affected by the fertility of the soil, i.e. the inherent capacity of the soil to release nitrogen to the crops in a readily assimilable form. The fertility of the soil thus depends on the rate of mineralization of organic nitrogen, that is the rate of gross N-mineralization. This is why it is important to provide an accurate estimate of this rate: It significantly influences the amount of fertiliser that needs to be applied to a field of crops. Furthermore, nitrogen-fertiliser demand and crop nitrogen-demand can be regarded as synonyms for the additional nitrogen fertiliser requirement of a certain crop on a particular field.

If insufficient amounts of minerals other than nitrogen were frequently found also to lead to growth limiting effects, the mass balance in the soil of such minerals would also be essential in fertiliser planning. However, nitrogen is very often the single most important growth limiting factor for most plants including agricultural crops. Accordingly, nitrogen must form an essential part of a fertiliser for crop production. It is a fact that the most important determinants of the amount of nitrogen-fertiliser required are the total amount of organic nitrogen present in a soil and the rate at which this organic nitrogen is converted to inorganic, i.e. plant assimilable nitrogen. Consequently, the rate of gross N-mineralization is not only the most important and significant parameter in fertiliser planning, it is also the most difficult process to include. Not surprising, N-mineralization is either not at all accounted for in conventional fertiliser planning, or alternatively, it is inaccurately accounted for due to a complete lack of methods providing a reliable and accurate determination of the rate of gross N-mineralization of a soil.

This lack of reliable and accurate methods poses a serious problem to the farmer: How to determine accurately the approximate amount of nitrogen-fertiliser to apply to a field of crops in order to facilitate an optimal crop growth and at the same time preventing e.g. nitrate leaching? The farmer may well acknowledge that a significant amount of nitrogen is already present in the soil, but how much nitrogen is present in a readily assimilable form. What is the rate of formation of inorganic nitrogen? Which legislative regulations impose restrictions on the use of nitrogen-fertilisers for the particular soil conditions and crops in question in order to prevent nitrogen leaching? The questions put to the farmer are many—the answers surprisingly few and difficult to produce.

In summary, the fundamental information needed to facilitate an optimal fertiliser application is the knowledge of the amount of nitrogen required by the various crops on a particular field. The prime determinants of potential crop yield and thus crop nitrogen demand are the inherent crop properties, the nature of the soil and its inherent capacity to supply plant available nitrogen to the crops. This capacity is also termed the N-mineralization rate. N-mineralization in agricultural soils is therefore of fundamental agronomic importance. N-mineralization, i.e., the soils inherent capacity to supply nitrogen, is thus the prime determinant of additional fertiliser nitrogen demand (crop nitrogen demand).

It is a fact that nitrogen-fertilisers—if used excessively—will not only facilitate plant growth, but also lead to an undesirable build-up of nitrogen in the environment. Inorganic nitrogen-compounds such as nitrate, ammonia and nitrogen oxides may cause detrimental effects to both human health and sensitive, aquatic ecosystems. It is thus desirable to adjust the use of nitrogen-fertilisers to crop nitrogen demands and thus supplement a soil with an amount of nitrogen strictly required for crop growth. Also, from a production cost point of view, the purchase of nitrogen-fertilisers represent a major cost in contemporary agricultural productions, and the farmer has an economic incentive in trying to optimise the use of nitrogen-fertiliser. Further incentives for optimising fertiliser planning includes avoiding a possible tax on excessive use of fertilisers.

In order to reduce the amount of nitrogen leaching out into subsoil waters, mandatory crop rotation and fertiliser planning is required so as to avoid excess fertilisation and to further ensure, that the required minimum utilisation efficiencies of animal manures are achieved. To this purpose, farmers must each year submit a crop rotation plan, a fertiliser plan including an estimation of the need for nitrogen application according to economically optimal dosages, and specifications as to how the fertiliser requirement is being met by means of e.g. animal manure, other organic manures including waste products, or by the application of commercial fertilisers. The plans must also include a sketch map indicating the location and size in hectares of individual fields.

The total fertiliser application including the effective fraction of nitrogen contained in the animal manure must not exceed the crop demand set by the authorities. Moreover, the minimum utilisation efficiency of nitrogen in animal manure and other organic fertilisers established by authorities must be observed.

When the farmer prepares crop rotation and fertiliser plans, the nominal values for crop yield and nitrogen crop demand set by a number of crops by the authorities, must be applied. Nominal crop yields and thus nominal crop nitrogen demands for each crop in a variety of crop rotation plans may be introduced as a function of e.g. climate, soil type and access to irrigation. The nominal value of nitrogen application must also adhere to the limits established by an annual nitrogen prognosis. This prognosis is based on the so called "square grid net" of representative sample points covering regions, where the soil mineral nitrogen content (inorganic nitrogen) is assessed. Typical corrections are in the order of plus or minus 5 kg nitrogen per hectare. In more extreme years the correction may average 10 to 15 kg nitrogen per hectare.

Legislation has been introduced in the European Union in order to reduce nitrate pollution. Directive 91/676/EEC, the so-called "Nitrate Directive", has the clearly stated objective to "reduce water pollution caused or induced by nitrates from agricultural sources and prevent further such pollution".

Precision farming systems have been introduced in order to adjust the amount of a fertiliser to a specific soil condition and a specific crop demand in each subsection of a field, as compared to the conventional "blanket dressing" of fertilisers. The overall objectives of introducing such systems are partly aimed at reducing the amount fertiliser used, and thus improving the economics of the agricultural production, and partly aimed at achieving a more efficient application of the fertiliser in order to reduce the amount of nitrogen leaching.

Precision farming systems are presently based on indications of e.g. crop nitrogen-demand in subsections of an agricultural field. The subsections may have been introduced in order to facilitate the use of a so-called global positioning system (GPS). Accordingly, precision farming systems and the following adjustment of fertiliser application by means of a GPS are novel initiatives introduced by industry and farmers in order to try to optimise the use of nitrogen-fertilisers. However, the problem associated with the use of presently available precision farming systems is the lack of a simple and easy soil test to actually measure crop nitrogen demand. The direct result of using precision farming systems is the generation of a digital map of an agricultural field, which enables the farmer to use advanced fertiliser spreaders equipped with GPS and a personal computer (PC) in order to adjust fertiliser application in accordance with the nitrogen-content of a particular grid position and the specific crop nitrogen-demand for that grid position.

The N-mineralization process is mediated by a wide array of microorganisms present in the soil. Initially, such microorganisms will degrade nitrogen-containing polymers and macromolecules to nitrogen-containing oligomers and monomers. Some of these degradation products will be taken up and metabolised via, in principle, many different metabolic pathways present in different species of soil microorganisms. Further degradation products, such as nitrate, ammonia and urea, are generated by the soil microbial metabolism. Some of the products undergo further microbial and/or enzymatic processing. Examples are e.g. the uptake of released urea by some soil microorganisms (and the subsequent, intracellular metabolism of urea under the formation of e.g. ammonia), and the extracellular, enzymatic conversion of urea to carbon dioxide and ammonia, that takes place in the soil.

The microbially mediated process of N-mineralization is fundamentally a two step process. Firstly, the variety of organic nitrogen polymers present in soil is depolymerised by means of exoenzymes, i.e., enzymes produced by soil microorganisms and released into the soil. Such exoenzymes may e.g. hydrolyse large organic molecules to smaller molecules such as proteins to dipeptides or amino acids. Secondly, the smaller molecules are assimilated into microbial cells and further broken down by a set of microbial enzymes, which are internal to microbial cell walls. A detailed and conceptual model of N-mineralization is reviewed by Burton and McGill (1992). It is important to note that conventional wisdom dictates that the result of the N-mineralization is the direct formation of ammonia.

When urea is released into the soil solution it is rapidly converted to ammonia and $CO_2$ if not re-immobilised into other microbia cells. Likewise, ammonia may also be immobilised into microbial cells. Both mineralization and immobilisation may thus take place at the same time but, importantly, the two processes do not take place in the same micro-pore space in the soil—the processes are essentially united in time but separate in space.

The total outcome of the two opposite processes, i.e., the net production and net consumption of soil inorganic nitrogen (including urea) is termed net N-mineralization. It may initially appear to be the net production of plant available nitrogen which is important for plant production, and simple concepts of soil fertility have been based on measurements of net N-mineralization by means of long-term incubation under laboratory conditions of soil samples in order to assess the potential net N-mineralization. However, soil fertility, and thus the potential for plant production, is more appropriately described by rates of gross N-mineralization.

Soils not recently being supplemented with organic materials and characterised by steady-state rates of gross N-mineralization and immobilisation, may be balanced so that e.g. 2.5 kg nitrogen per hectare per day is immobilised and 7.5 kg nitrogen per hectare per day is mineralized, generating a net rate of N-mineralization of 5 kg nitrogen per hectare per day. Although supplementing the soil with organic materials having a high carbon (C) to nitrogen (N) ratio, such as e.g. straws and stubbles plowed into the soil, no doubt stimulates N-immobilisation for some period of time, the process of N-immobilisation is confined to micropores with undecomposed plant material having a high CIN ratios. Gross N-mineralization, on the other hand, is widespread among micro-pores because soil organic matter (SOM) with a C/N ratio of ca. 10 is present in large amounts such as in the order of 5000 kg nitrogen per hectare.

Furthermore, the microbial cells produced as a result of the supplemented organic material will eventually die and contribute to the SOM substrate pool available for other microorganisms and, eventually, it will be mineralized. Accordingly, previously immobilised nitrogen-compounds will also be released into the soil and thus, in general terms, it may be stated that immobilisation of nitrogen in soil is confined in space and time, whereas the process of gross N-mineralization is a continuos process related to the total content and plant availability of SOM.

The sustained production in natural and managed ecosystems relies on replenishing the soil of nutrients removed herefrom by crop harvest, leaching, or by other processes. While natural ecosystems thrive because of well established nutrient cycling mechanisms, the cornerstone of stable agricultural ecosystem is replenishment of nutrients by either organic or inorganic fertilisers. The need to use fertilisers and the open type nutrient cycling in contemporary agricultural systems pose a particular challenge to the production of economically optimal crop yields while at the same time ensuring a minimal leaching to the surrounding environment.

SUMMARY OF THE INVENTION

The present invention relates to a method for determination of the gross N-mineralization rate of a first soil sample, said method comprising the steps of
  i) determining the activity of a microbial enzyme of a functional ornithine acid cycle contained in said sample,
  ii) determining
    a) the activity of said enzyme in a second, predetermined soil sample, and
    b) the corresponding gross N-mineralization rate of said second, predetermined soil sample, and
  iii) determining the gross N-mineralization rate of said first soil sample on the basis of the gross N-mineralization rate corresponding to said activity determined in step ii).

Hereby, there is provided a quick and reliable method for measuring the gross N-mineralization rate of a soil sample. The method exploits that a microbial enzyme activity of a functional ornithine acid cycle present in said sample was surprisingly found to be directly correlatable with the rate of gross N-mineralization of that same sample.

Accordingly, the total amount of inorganic nitrogen available for plant uptake can be calculated based on a determination of the gross N-mineralization rate of a soil sample. The gross N-mineralization rate represents the overall conversion in the soil of nitrogen present in organic material to inorganic nitrogen such as e.g. nitrate and ammonia. Gross N-mineralization rates determined by using the method of the invention provides the farmer with a reliable estimate of the rate of inorganic nitrogen released into the soil, i.e. the amount of inorganic nitrogen measured e.g. in gram per kilogram soil per hour, or, in agronomic terms, e.g. in gram per hectare over a growing season.

In another aspect of the invention there is provided a method of determining the amount of fertiliser to apply to a soil. In yet another aspect there is provided a test-kit for determining the gross N-mineralization rate of a soil sample.

More specifically, the invention exploits the surprising discovery that the nitrogen of essentially all nitrogen-containing substances present in a soil, when being metabolised by soil microorganisms, is released via an arginine-urea metabolic pathway. The essence of the arginine-urea pathway is the enzymatic conversion of arginine to ornithine acid under the release of urea. The arginine-urea pathway forms part of a "functional ornithine acid cycle", as the arginine-urea pathway leads to the regeneration of ornithine acid, which can then reenter the cycle and be converted to arginine.

Accordingly, any cyclical event involving a number of enzymatic steps leading to 1) the formation of arginine from ornithine acid and an ammonia donor and 2) the catalysis of arginine under the formation of urea and ornithine acid, may thus be termed a "functional ornithine acid cycle". One example of a functional ornithine acid cycle is the conventional urea cycle cited in standard textbooks. However, variations of a conventional urea cycle may well exist among microbial soil organisms and such variations are intended to be comprised by the term "functional ornithine acid cycle".

Consequently, the gross rate of N-mineralization can be measured by determining the "flow" of nitrogen through a functional ornithine acid cycle such as e.g. the conventional urea cycle. More particularly, the invention provides a quick, reliable and simple measure of said gross rate of N-mineralization by determining in a soil sample the content of an enzyme such as e.g. arginine deaminase (arginase), which is responsible for catalysing the deamination of arginine and the subsequent formation of urea and ornithine acid.

The method according to the invention can be used e.g. in determining the amount of nitrogen-containing fertiliser to be applied to a field of agricultural crops. This determination greatly facilitates the introduction of important new precision farming techniques because detailed mapping of N-mineralization rates, and thus crop nitrogen demands, within any subsection of any field, is now rendered possible. Although such precision farming technologies are already commercially available, a significant breakthrough of such systems awaits the development of a simple and inexpensive soil test such as the present N-mineralization test.

In summary, the gross N-mineralization rate facilitates a determination of the release of plant available nitrogen. This determination enables the farmer to include the release of nitrogen in fertiliser planning. Accordingly, the inclusion of a reliable N-mineralization rate facilitates the farmer in determining the amount of fertiliser to apply to a soil. If widely used among farmers, the present method will lead to a significant overall reduction in the amount of nitrogen-fertilisers being used and this will subsequently lead to a considerable reduction of e.g. nitrate leaching.

μg NH4+-N/gram soil×hour]. The arginase enzyme exhibits simple Michaelis-Menten kinetics and $V_{max}$ and $K_m$ were determined as 2.38+/−0.03 [μg NH4+-N/gram soil×hour] and 0.05+/−0.004 mM, respectively.

Figure 2:
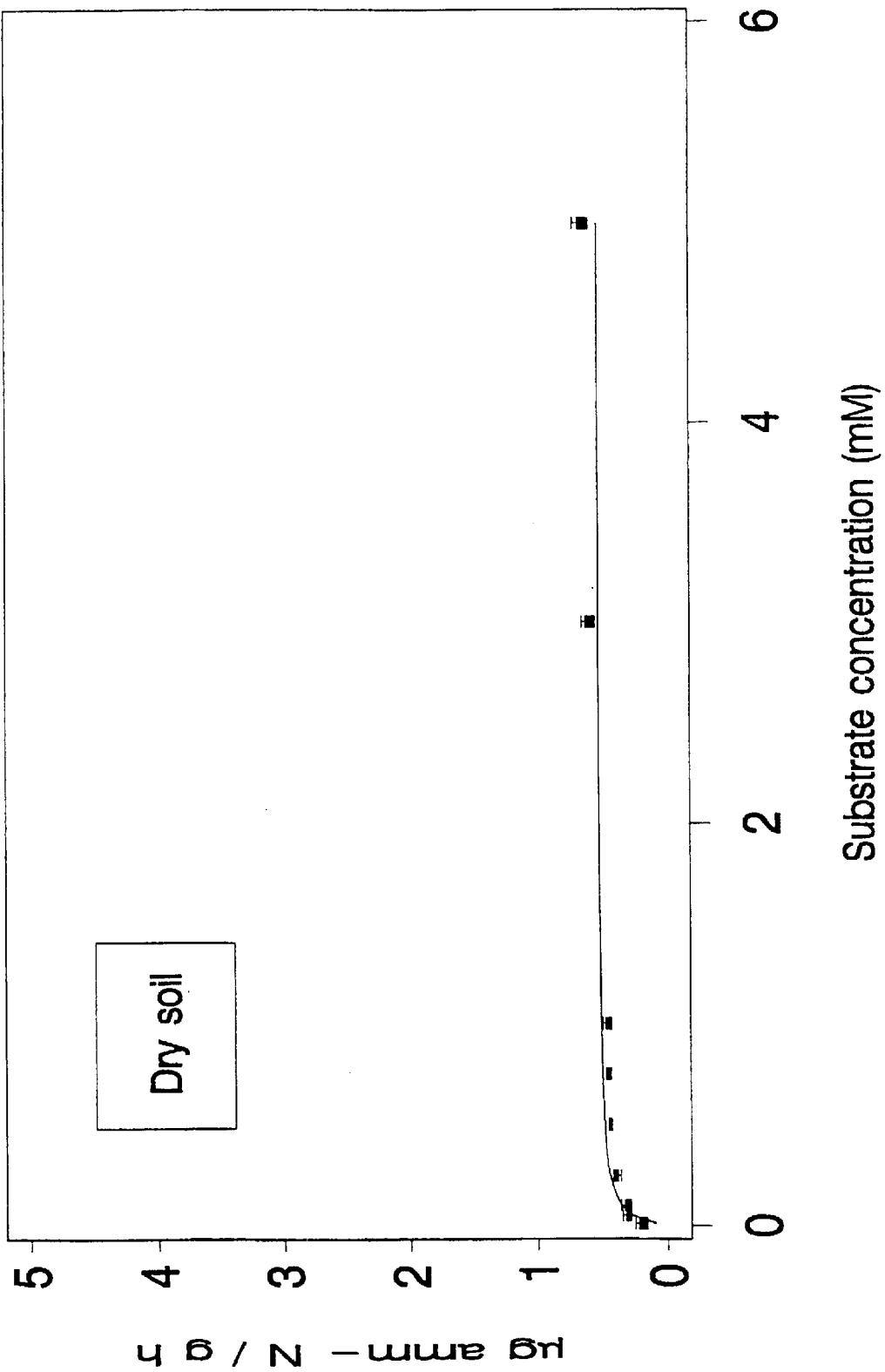
Figure 3:
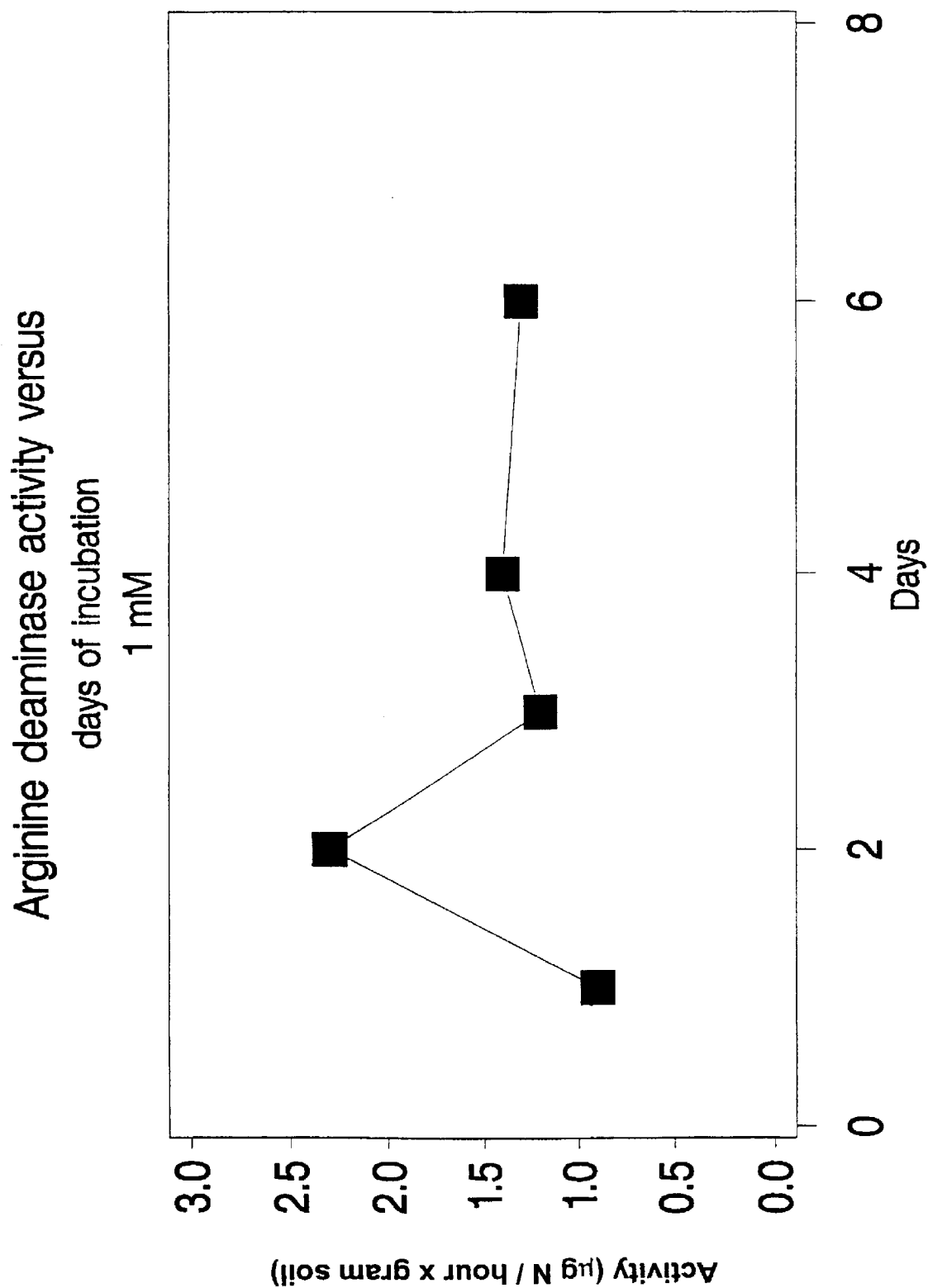
Figure 4:
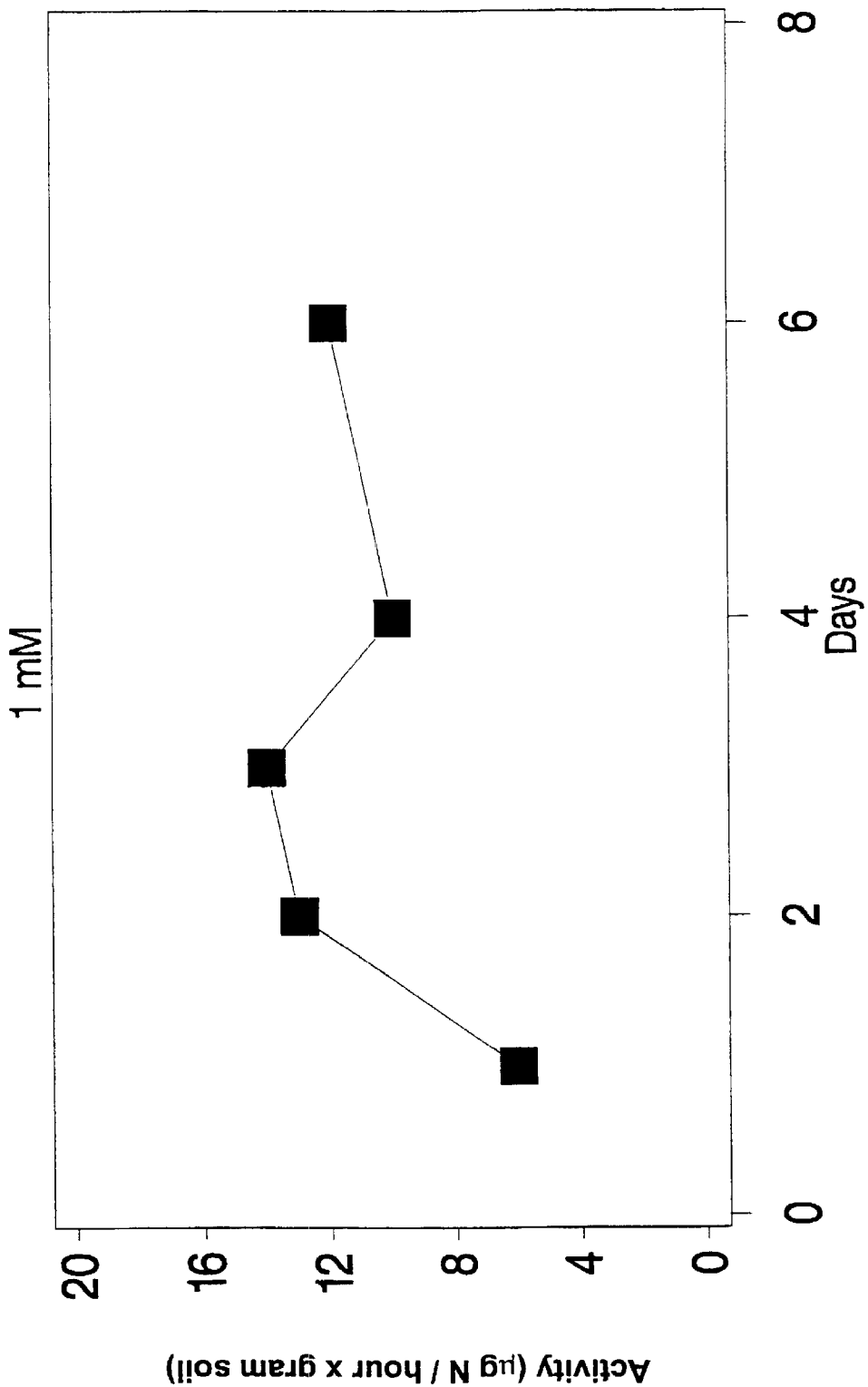
Figure 5:
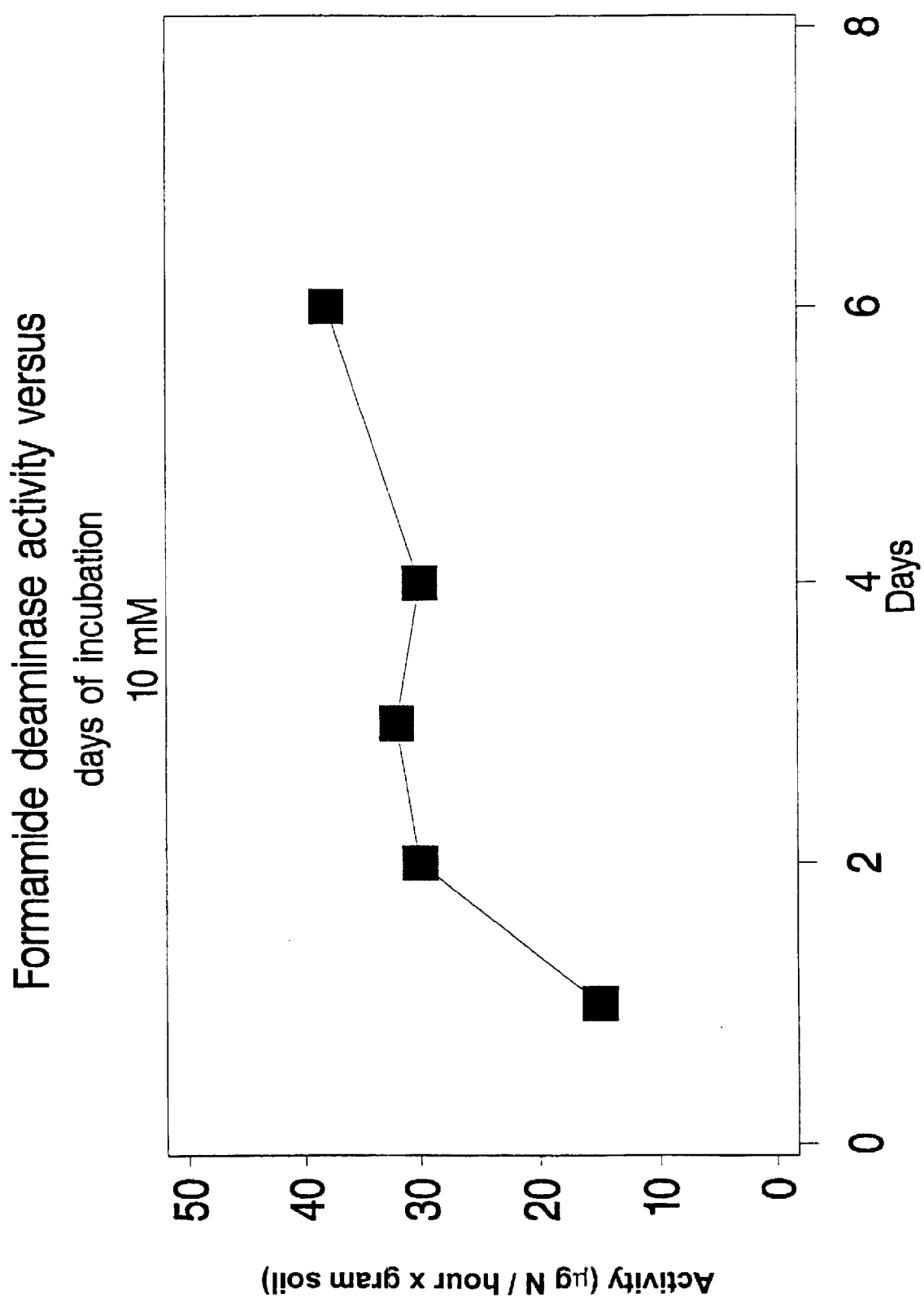
Figure 6:
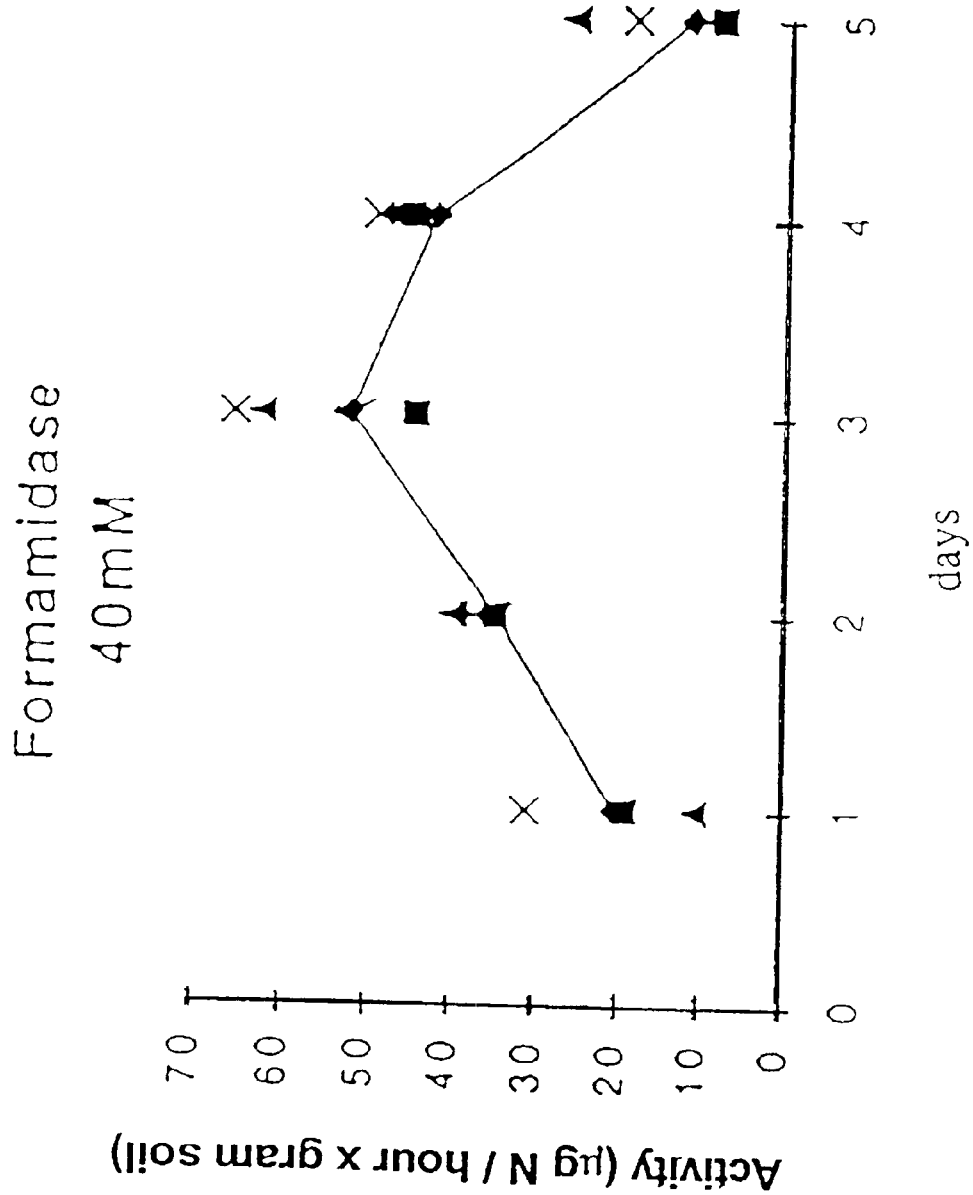
Figure 7:
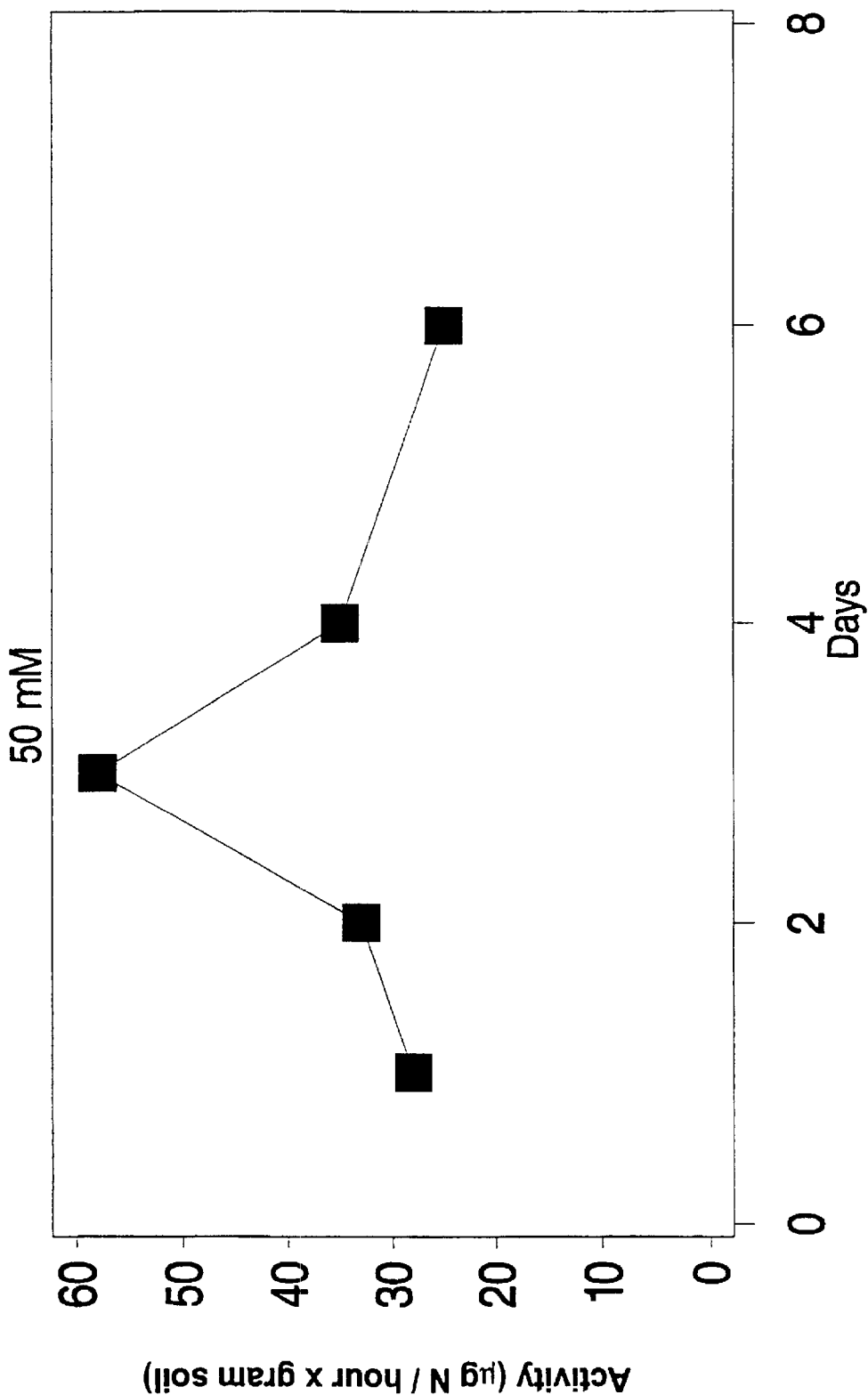

FIG. 2 illustrates the amount of ammonium generated per gram dry soil per hour [μg NH4+-N/gram soil×hour] as a function of different arginine concentrations [mM]. A maximum conversion of arginine to ammonium is achieved, when the concentration of arginine is 0.5 mM or higher. The maximum conversion generates approximately 0.6 pg NH4+-N per gram soil each hour [0.6 μg NH4+-N/gram soil×hour]. The arginase enzyme exhibits simple Michaelis-Menten kinetics and $V_{max}$ and $K_m$ were determined as 0.53 +/−0.02 [μg NH4+-N/gram soil×hour] and 0.05+/−0.01 mM, respectively. Although the dry soil reveals a considerably lower enzyme activity, simple Michaelis-Menten kinetics are still achieved.

FIGS. 3–7 illustrate a comparison of the kinetics of two enzymes, arginase and formamidase, assayed under directly comparable conditions. A sample of barley soil was dried (5% water) ad divided into five subsamples, A to E, on day 1 of the experiment. Formamide, a substrate of formamidase, was added to subsamples A to D to final concentrations of 1 mM, 10 mM, 40 mM and 50 mM, respectively. Arginine was added to subsample E to a final concentration of 1 mM. All subsamples were rewetted on day 1 by adding water to a final concentration of ca. 15%. The data indicate that formamidase activity is not readily correlatable, or indeed correlatable in any meaningful way, with the process of N-mineralization. In contrast, the data generated for subsample E, the subsample assayed for arginase activity, clearly shows that arginase activity, measured by the formation of $NH_4^+$ ions [μg $NH_4^+$-N/gram soil×hour], may well be correlated with the rate of gross N-mineralization. Once the initial "boost" of N-mineralization mediated by microbial enzymatic activities has ceased, a steady state rate of N-mineralization occurs, as indicated by the essentially uniform arginase activity measured during on days 3 to 5.

The data depicted is arginine deaminase activity versus days of incubation for 1 mM arginine (FIG. 3), and formamide deaminase activity for 1 mM (FIG. 4), 10 mM (FIG. 5), 40 mM (FIG. 6) or 50 mM (FIG. 7) of formamide.

Figure 8:
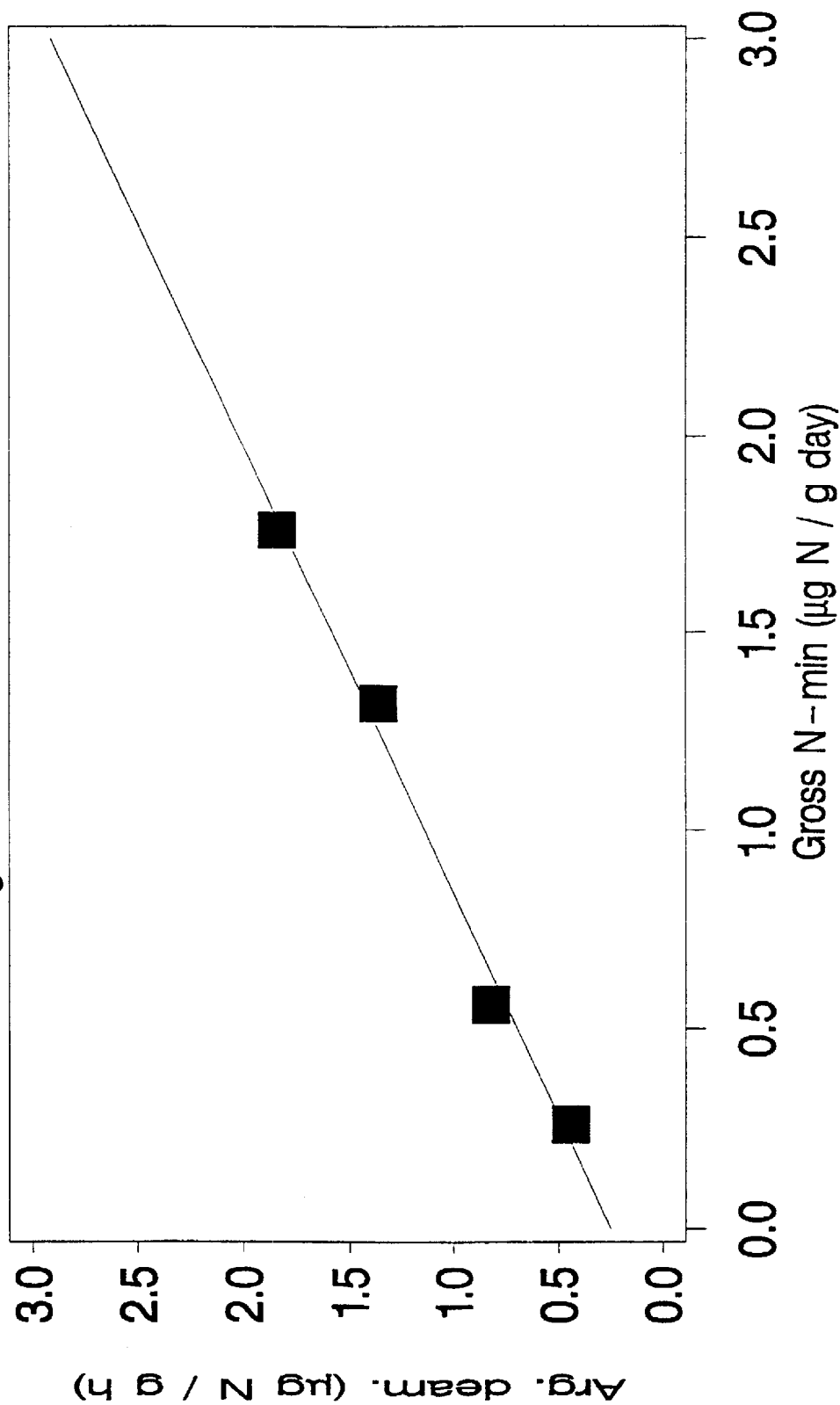

FIG. 8 illustrates correlation of arginase activity, measured as μg $NH_4^+$-N generated per gram soil per hour, with a rate of gross N-mineralization, measured as μg nitrogen mineralized per gram soil per day.

Figure 9:
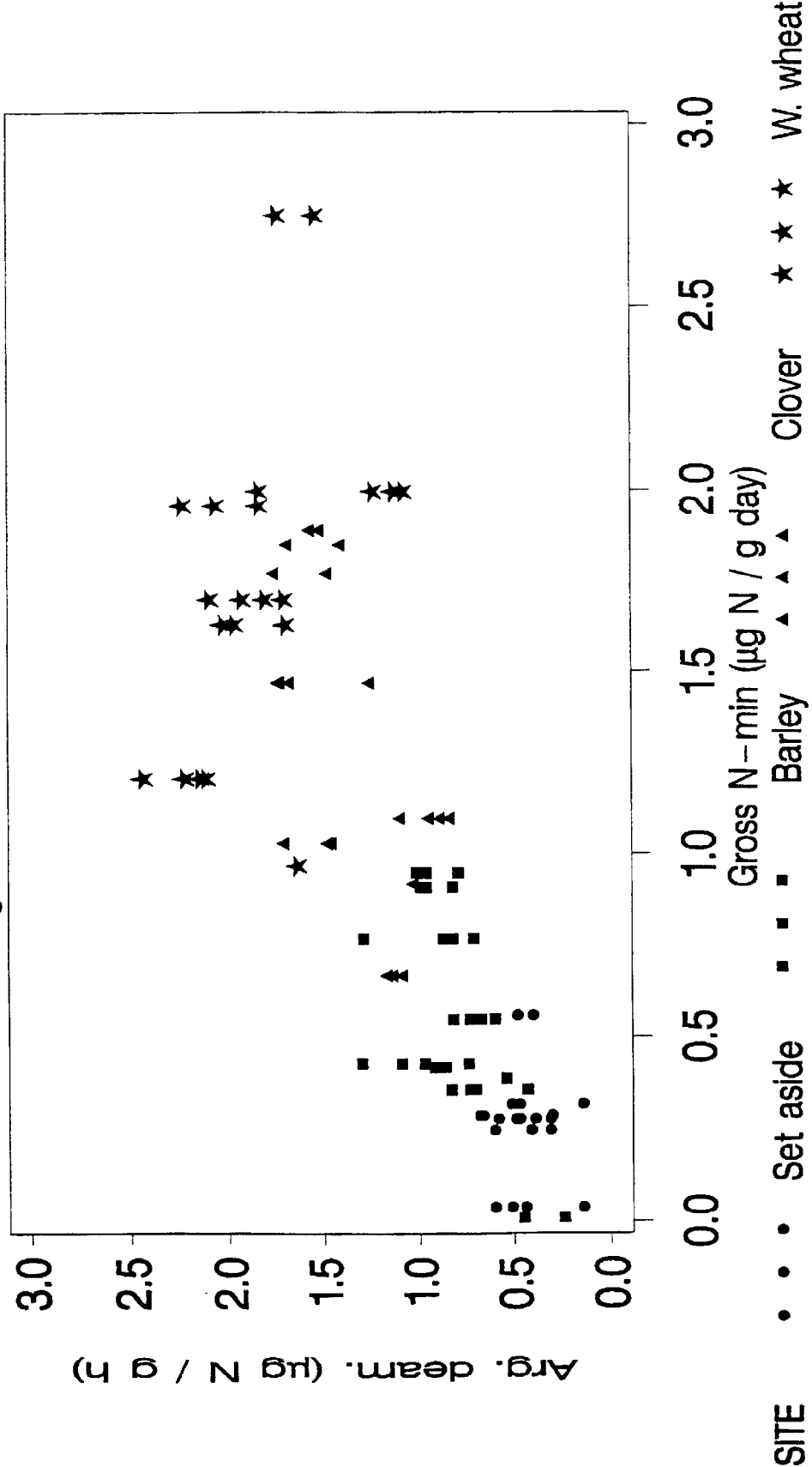

FIG. 9 illustrates the four different types of soils used and the different rates of gross N-mineralization associated with each of these soils. The soils are set aside soil (circles) and soils cropped with barley (squares), clover (triangles) and winter wheat (stars), respectively. Average corresponding values of arginase activity and gross N.mineralization rates were produced for each of the soils, and these averages are presented in FIG. 8. The measurements of arginase activity and the calculation of gross N-mineralization rates by means of an isotope dilution technique were performed during the growth season of 1995, i.e. during the months of May, June and July.

Figure 10:
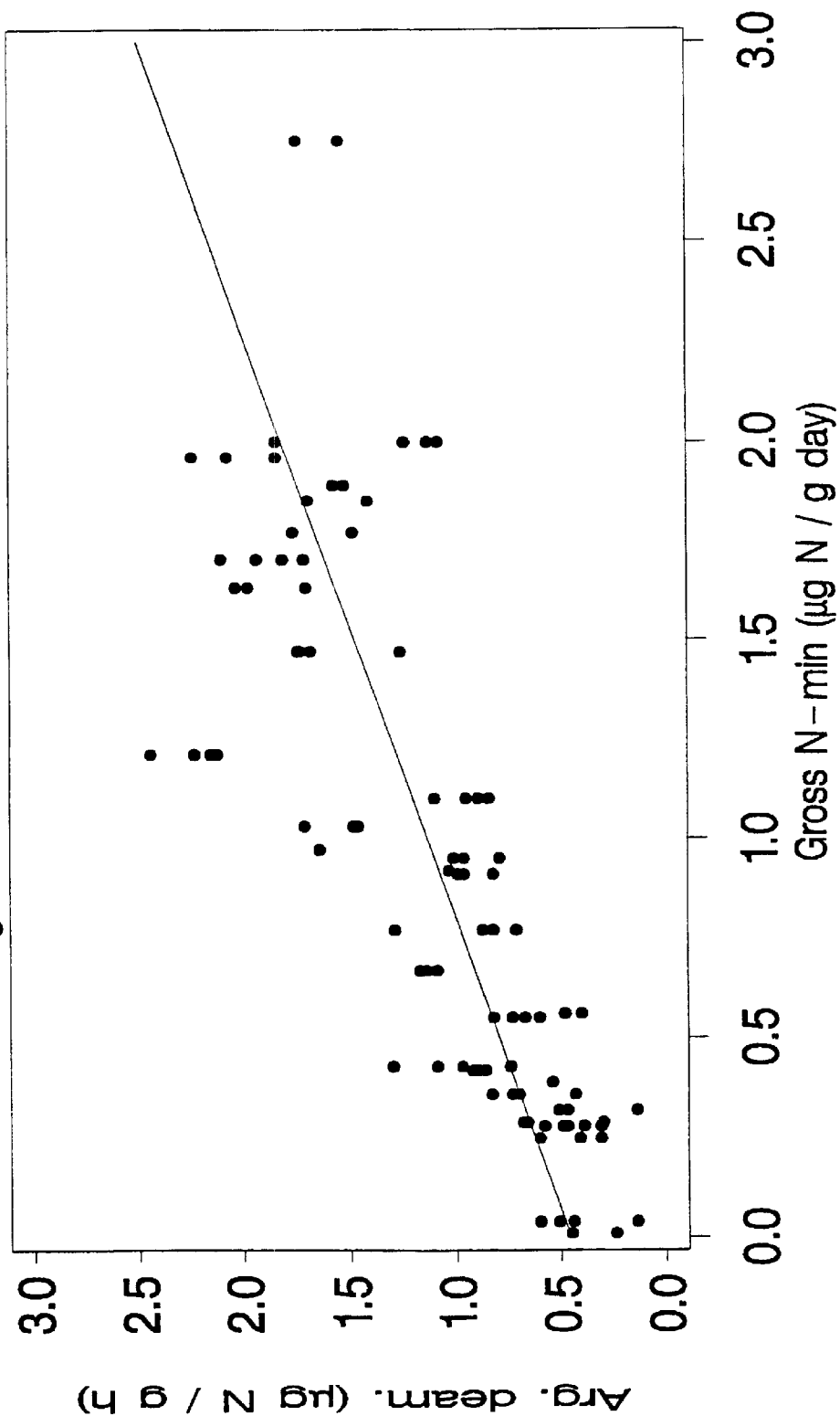

FIG. 10 illustrates the relationship between arginase activity and rate of gross N-mineralization for the entire set of data illustrated in FIG. 9. NO averages were calculated. Instead, the entire set of data were pooled in order to seek a correlation based on sets of data from each soil.

Figure 11:
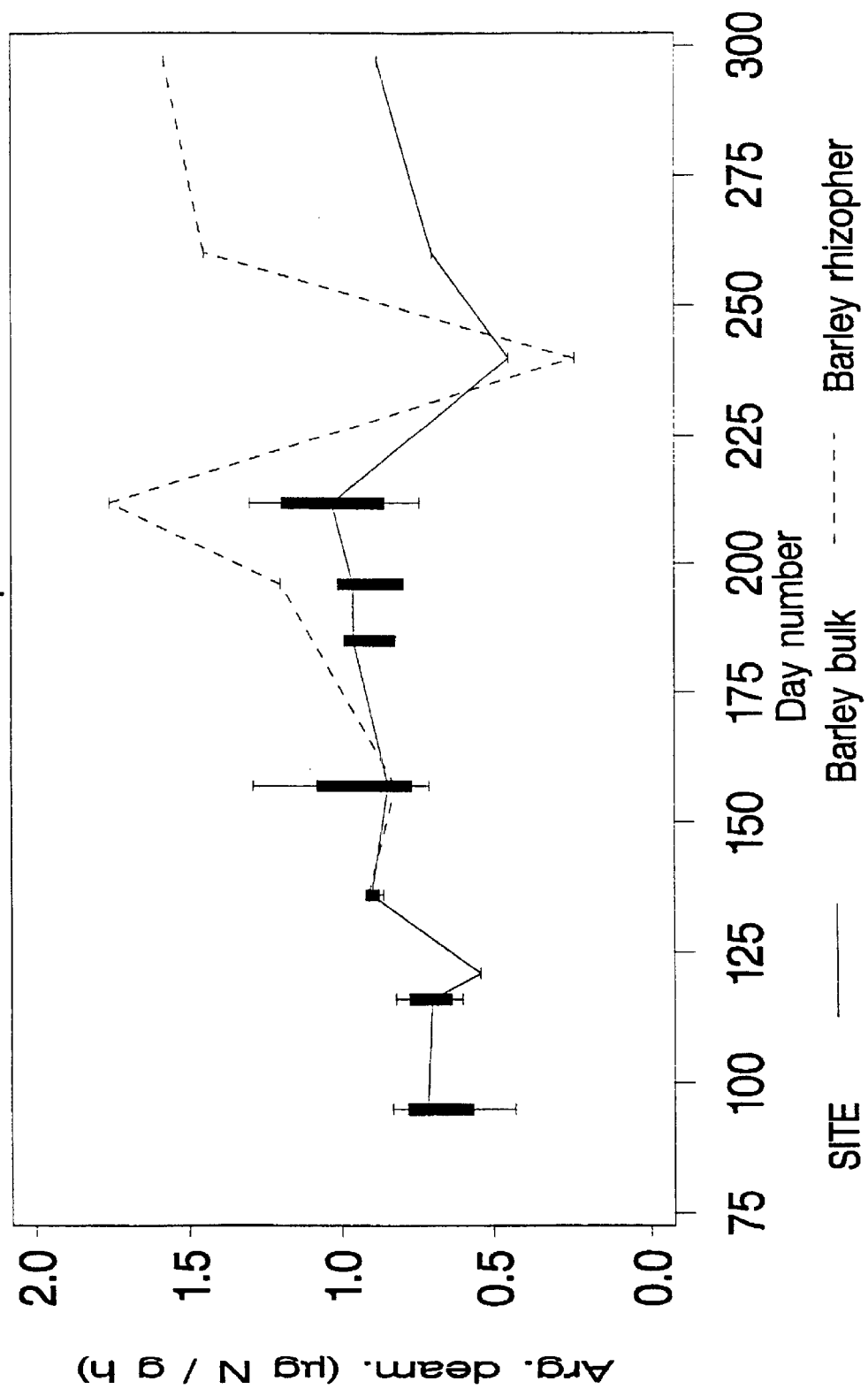

FIG. 11 illustrates the seasonal variations of arginase activity (μg NH4+/gram soil×hour) observed in bulk soil and rhizophere barley soil throughout a growth season. Day 1 is Jan. 1, 1995.

Figure 12:
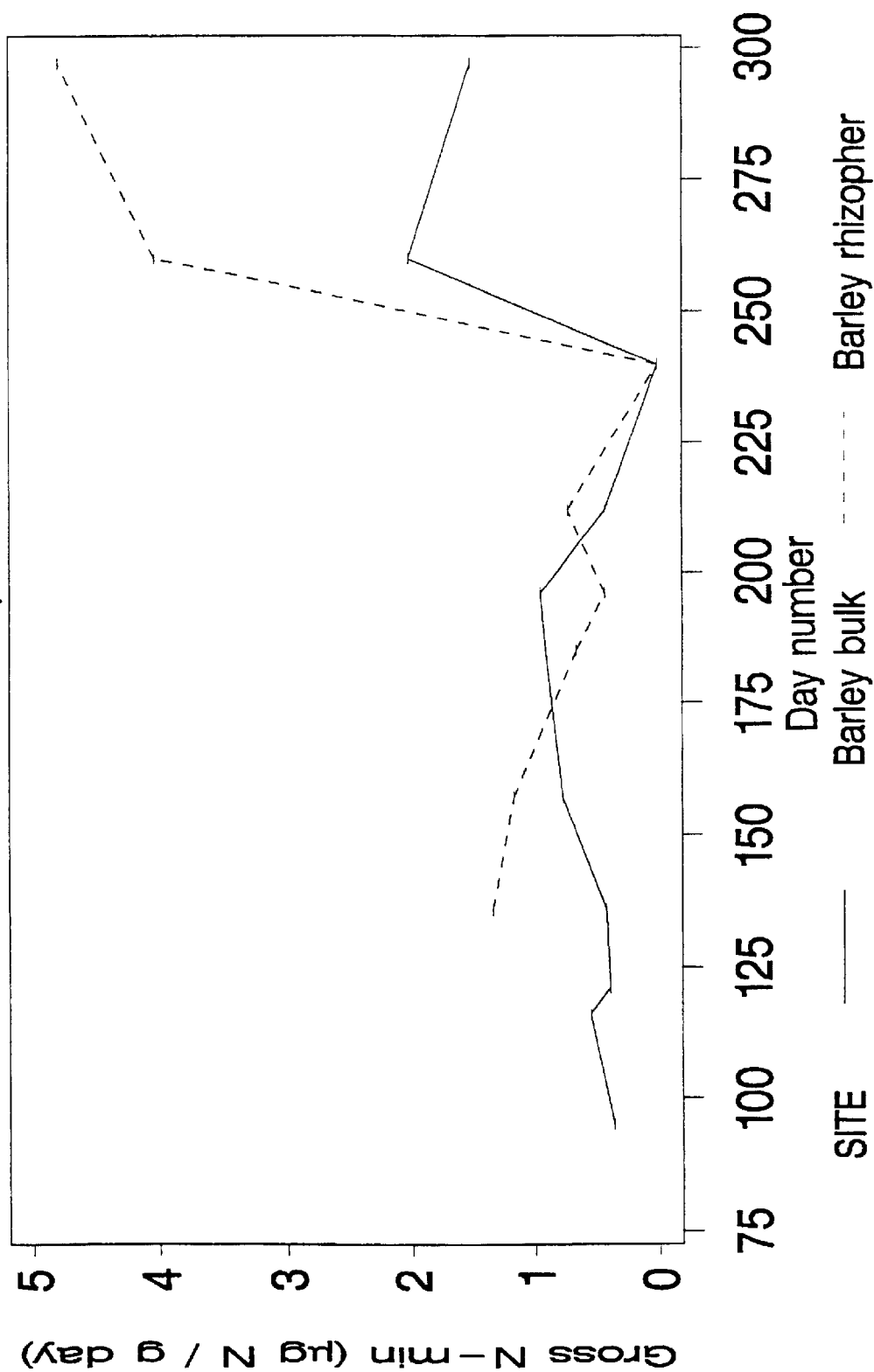

FIG. 12 illustrates the seasonal variations of the gross N-mineralization rates (μg nitrogen/gram soil×day) observed in bulk soil ad rhizophere barley soil throughout a growth season. Day 1 is Jan. 1, 1995.

Figure 13:
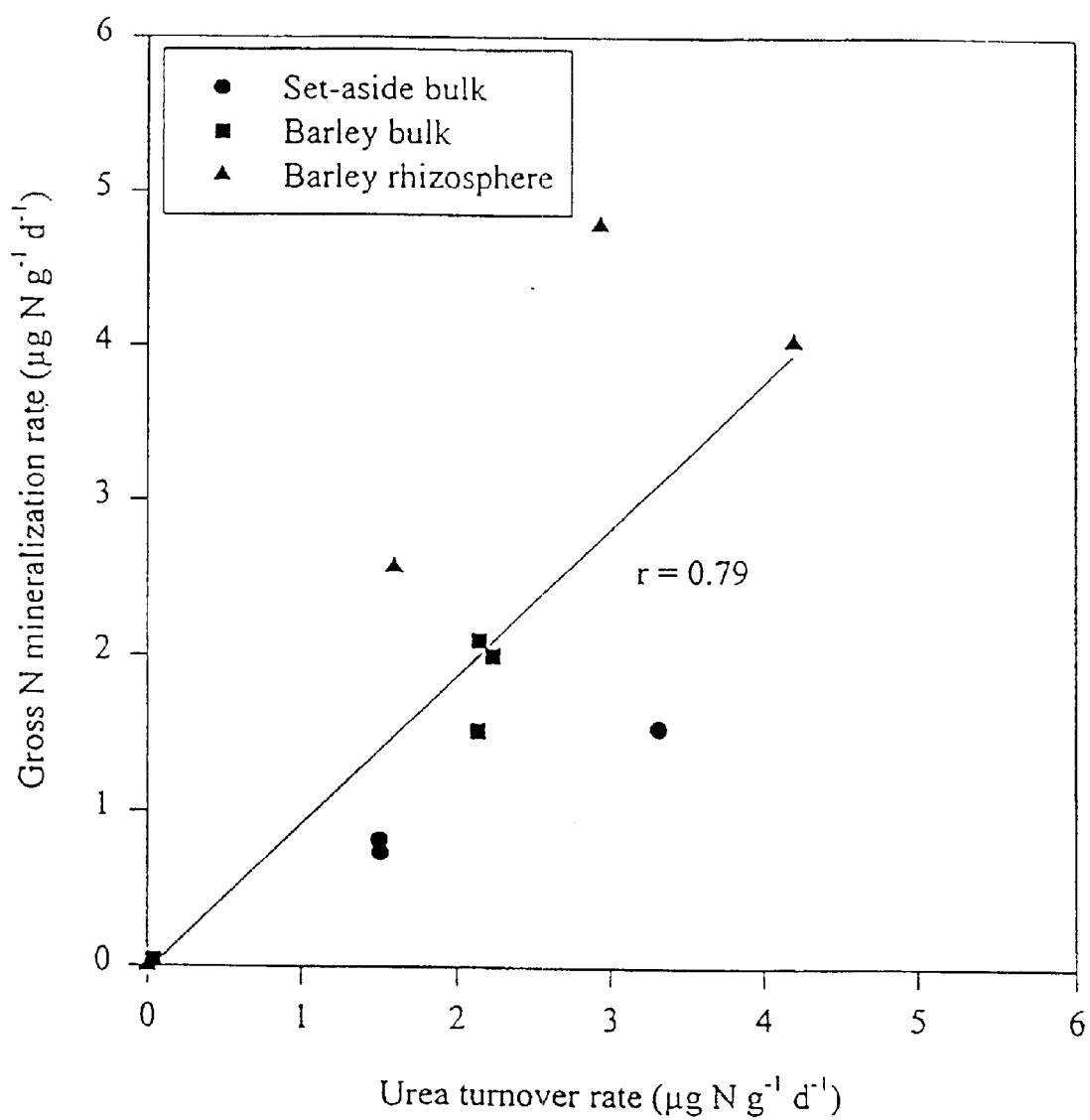

FIG. 13 is based on the results presented in Table 1 and illustrates a correlation of the gross N-mineralization rate with the urea turnover rate for each of three different types of soil analysed.

Figure 14:
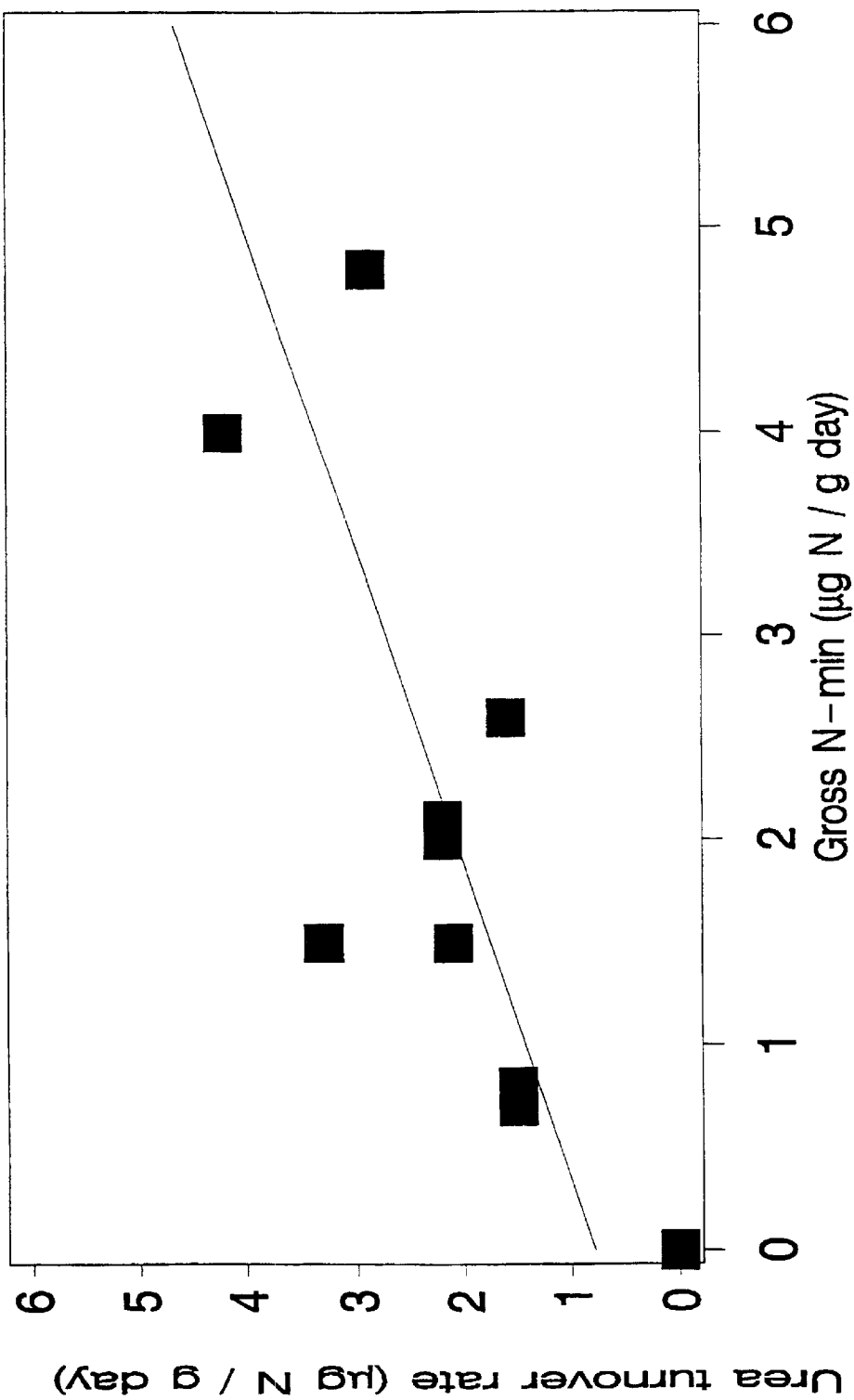

FIG. 14 is based on the results presented in Table 1 and illustrates a correlation of the gross N-mineralization rate with the urea turnover rate.

Figure 15:
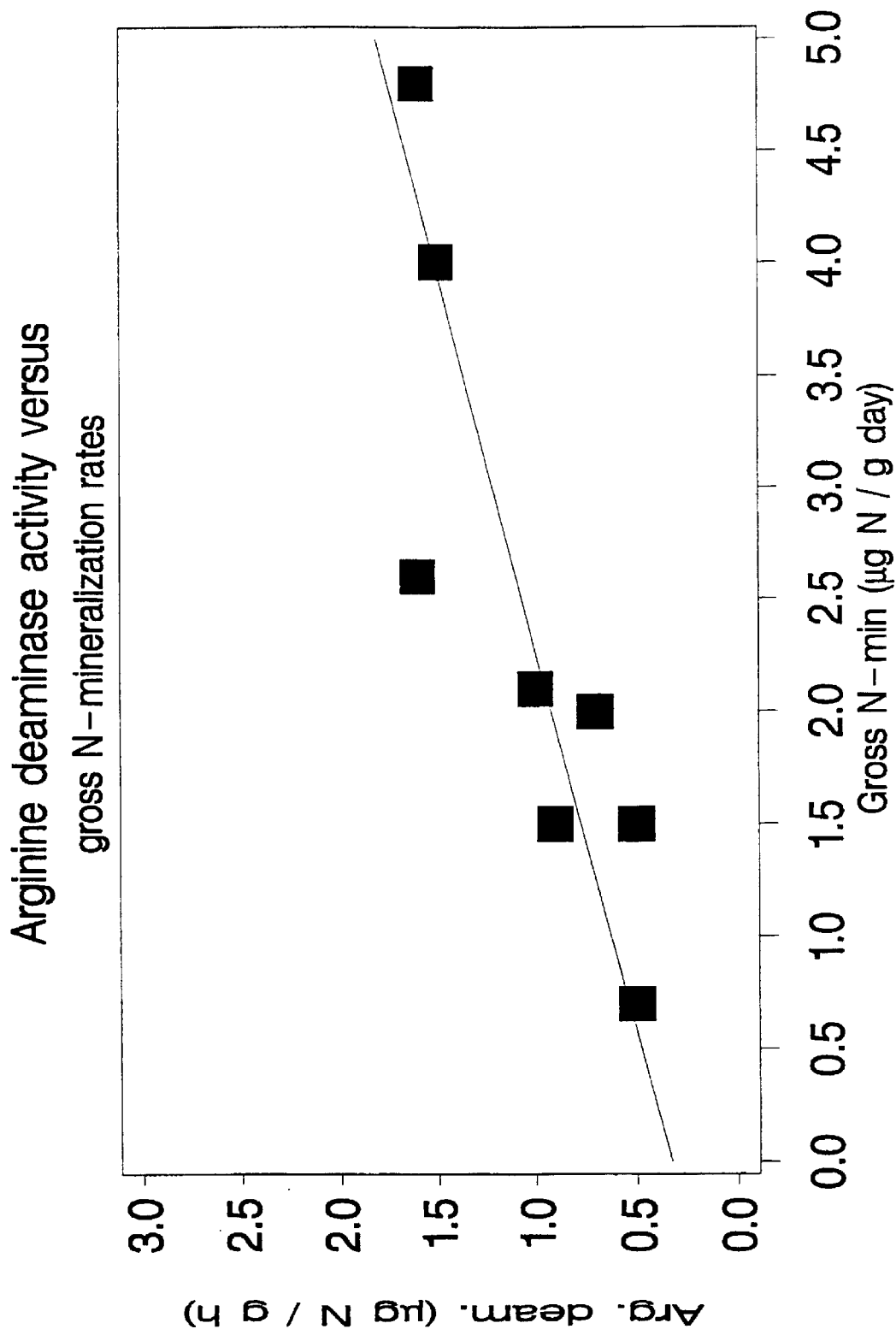

FIG. 15 is also based on the results presented in Table 1 and illustrates a correlation of arginase activity with gross N-mineralization rate for each of the three different types of soil listed in Table 1.

DETAILED DESCRIPTION OF THE INVENTION

In a first aspect, the present invention relates to a method for determination of the gross N-mineralization rate of a first soil sample, said method comprising the steps of
i) determining the activity of a microbial enzyme of a functional ornithine acid cycle contained in said sample,
ii) determining
 a) the activity of said enzyme in a second, predetermined soil sample, and
 b) the corresponding gross N-mineralization rate of said second, predetermined soil sample, and
iii) determining the gross N-mineralization rate of said first soil sample on the basis of the gross N-mineralization rate corresponding to said activity determined in step ii).

In one embodiment the functional ornithine acid cycle is a conventional urea cycle and the enzymatic activity is consequently the activity of an enzyme forming part of such a conventional urea cycle. Examples of such enzymes are arginine deaminase (arginase), ornithine transcarbamylase, argininosuccinic synthetase and argininosuccinic cleavage enzyme.

It is particularly preferred to determine, in step i) of the above method, the activity of the enzyme arginine deaminase (arginase). This activity may be determined by assaying a soil sample by means of a standard assaying technique. Such a technique may involve measuring the product formation catalysed by the enzyme or a compound easily correlatable with such a product.

In one preferred embodiment, the activity of the arginase enzyme is assayed and the activity of the arginase enzyme is thus determined by measuring the amount of $NH_4^+$ ions formed under suitable incubation conditions. The amount of ammonium ions formed over time may be measured e.g. essentially according to the method of Verdouw et al. (1977) described in Water Research, vol. 12, pages 399 to 402.

In a preferred embodiment, the enzyme of the method mediates at least one reaction selected from the group consisting of arginine deamination and urea formation, such as e.g. an enzyme mediating arginine deamination or an enzyme mediating urea formation.

In an even more preferred embodiment, the enzyme belongs to an arginine-urea pathway, i.e. a pathway consisting of one step or a number of steps, such as e.g. one step or a number of steps mediating the enzymatic conversion of arginine under the formation of urea.

In another embodiment the enzyme exhibits simple Michaelis-Menten kinetics. The person skilled in the art will readily be able to determine, if an enzyme exhibits simple Michaelis-Menten kinetics. Such an enzyme will e.g. have to obey or substantially obey the kinetics described herein above. The enzyme may also exhibit Michaelis-Menten kinetics selected from the group consisting of zero order kinetics, first order kinetics, second order kinetics and combinations hereof. Likewise, the person skilled in the art will readily be able to recognise such zero order kinetics, first order kinetics, and second order kinetics based on the results of a suitable enzymatic assay. It is particularly preferred that the enzyme exhibits Michaelis-Menten first order kinetics.

In one preferred embodiment, the enzyme has a Michaelis-Menten constant, $K_m$, measured in mM (millimolar), of less than 1.0, such as 0.90, for example 0.80, such as 0.70, for example 0.60, such as 0.50, for example 0.40, such as 0.30, for example 0.25, such as 0.20, such as 0.15, for example 0.10, such as 0.05, for example 0.02, such as 0.01, for example 0.005, such as 0.002, for example 0.001.

In another preferred embodiment, the maximum velocity of the reaction catalysed by the enzyme, $V_{max}$, measured as [$\mu g$ $NH_4^+$-N/gram soil×hour], is less than 4.0, such as 3.5, for example 3.0, such as 2.75, such as 2.5, such as 2.38, for example 2.25, such as 2.0, for example 1.5, such as 1.25, for example 1.0, such as 0.75, such as 0.53, for example 0.35, such as 0.25, for example 0.2.

The soil sample may in a preferred embodiment of the invention have a weight of less than 10 grams, such as 5 grams, for example 2 grams, such as 1 gram, for example 0.5 gram, such as 0.2 gram, for example 0.1 gram, such as 0.05 gram, such as less than 0.001 gram. The soil sample may be selected from the group consisting of bulk soil, rhizosphere soil and combinations hereof.

In a particularly preferred embodiment, the activity of the enzyme is determined by an assaying technique. The duration of said assay is preferably less than 4 hours, such as 3 hours, for example 2 hours, such as 1.5 hours, for example 1 hour, such as 0.5 hour, for example 0.25 hour, such as less than 0.1 hour.

In another preferred embodiment, the gross N-mineralization rate is determined essentially by using a $^{15}NH_4^+$-dilution technique. One such $^{15}NH_4^+$-dilution technique is the $^{15}NH_4^+$-dilution technique of Blackburn (1979) described in Applied and Environmental Microbiology, vol. 37, pages 760–765.

The correlation of enzyme activity with gross N-mineralization rate may preferably be characterised by a Pearsson Correlation Coefficient and a corresponding level of significance. It is particularly preferred that said level of significance is at least 99.4%, such as 99.5%, for example 99.6%, such as 99.7%, for example 99.8%, such as 99.9%, for example 99.99%, and it is particularly preferred that said Pearsson Correlation Coefficient being at least 0.75, for example 0.77, such as 0.7913, for example 0.80, such as 0.83, for example 0.8558, such as 0.87, for example 0.90, such as 0.93, for example 0.96, such as 0.9740, for example 0.9949.

In another preferred embodiment, the correlatable relationship between said enzyme activity and said gross N-mineralization rate is expressed by means of a standard equation. The standard equation may be a substantially linear standard equation or it may be a non-linear standard equation. When the standard equation is a non.linear equation, it may be substantially without any local minima and/or local maxima.

In another aspect of the invention, there is provided a method for determining the gross N-mineralization rate of a soil sample, said method comprising the steps of i) determining the activity of a microbial enzyme of a functional ornithine acid cycle contained in said sample, ii) determining said gross N-mineralization rate of said soil sample by correlating said activity determined in step i) with said rate of gross N-mineralization by means of iii) a set of corresponding values or an established correlation generated by correlating the activity with the corresponding gross N-mineralization rate of a soil sample, said corresponding values and said correlation being generated by the steps of a) determining the activity of said enzyme contained in said sample, b) determining the rate of gross N-mineralization of said sample, c) generating corresponding values of said activity determined in step a) and said rate determined in step b), said corresponding values forming a correlatable relationship between said activity and said rate, and d) generating a correlation of said activity with said rate based on said corresponding values generated in step c).

In a further aspect the invention provides a method, cited in claim 26, for correlating a turn-over rate of urea to ammonium with a gross N-mineralization rate of a soil sample, said method comprising the steps of i) determining a urea turn-over rate of said sample, ii) determining a gross N-mineralization rate of said sample, iii) generating corresponding values of said urea turn-over rate determined in step i) and said gross N-mineralization rate determined in step ii), said corresponding values forming a correlatable relationship between said urea turn-over rate and said gross N-mineralization rate, and iv) establishing a correlation of said urea turn-over rate with said gross N-mineralization rate based on said corresponding values generated in step iii).

In one embodiment of this method, the urea turn-over rate is determined essentially according to a $^{14}C$-urea turn-over method such as e.g. the method of Lund and Blackburn (1989) as described in Journal of Microbiological Methods, vol. 9, pages 297–308.

The soil sample assayed in one embodiment has a weight of less than 10 grams, such as 5 grams, for example 2 grams, such as 1 gram, for example 0.5 gram, such as 0.2 gram, for example 0.1 gram, such as 0.05 gram, such as less than 0.001 gram. The soil sample may be either bulk soil, rhizosphere soil or combinations hereof.

In another preferred embodiment, the correlation of said urea turn-over rate with said gross N-mineralization rate is characterised by a Pearsson Correlation Coefficient and a corresponding level of significance, said level of significance being at least 98%, and said Pearsson Correlation Coefficient being at least 0.79, such as 0.82, for example 0.85, such as 0.88, for example 0.91, such as 0.94, for example 0.97. In another preferred embodiment the correlation is characterised by a Pearsson Correlation Coefficient of 0.6359 at the 94% level of significance.

In a particularly preferred embodiment, the correlatable relationship between said urea turn-over rate and said gross N-mineralization rate is expressed by means of a standard equation such as e.g. a substantially linear standard equation or a non-linear standard equation. The non-linear standard equation in one embodiment is substantially without any local minima and/or local maxima.

In an even further aspect of the invention, there is provided a method, cited in claim 35, for determining the gross N-mineralization rate of a soil sample by correlating said urea turn-over rate determined in step i) of claim 26 with said rate of gross N-mineralization by means of either a) using the set of corresponding values generated in step iii) of claim 26, or b) using the correlation established in step iv) of claim 26.

In one embodiment of this method, the gross N-mineralization rate is essentially directly proportional to said urea turn-over rate of said sample. In another embodiment, the gross N-mineralization rate is essentially equal to said urea turn-over rate of said sample.

Accordingly, it is possible to determine in claim 1 cited herein below, a gross N-mineralization rate by determining a urea turn-over rate and correlate this urea turn-over rate with the gross N-mineralization rate by means of the above-cited method of claim 35.

In another aspect of the present invention, there is provided a method, cited in claim 39, for determining the amount of fertiliser to apply to a soil, said method comprising the steps of i) determining a gross N-mineralization rate according to the method of claim 1, ii) including said gross N-mineralization rate determined in step i) in a calculation of the amount of fertiliser required to supplement said soil with an amount of nitrogen equal to the amount of nitrogen being mineralized, and iii) applying to said soil said amount of fertiliser calculated in step ii).

In yet another aspect of the present invention there is provided a method, cited in claim 40, for determining the amount of fertiliser to apply to a soil, said method comprising the steps of i) determining a gross N-mineralization rate according to the method of claim 25, ii) including said gross N-mineralization rate determined in step i) in a calculation of the amount of fertiliser required to supplement said soil with an amount of nitrogen equal to the amount of nitrogen being mineralized, and iii) applying to said soil said amount of fertiliser calculated in step ii).

In a further aspect there is provided a method, cited in claim 41, for determining the amount of fertiliser to apply to a soil, said method comprising the steps of i) determining a gross N-mineralization rate according to the method of claim 35, ii) including said gross N-mineralization rate determined in step i) in a calculation of the amount of fertiliser required to supplement said soil with an amount of nitrogen equal to the amount of nitrogen being mineralized, and iii) applying to said soil said amount of fertiliser calculated in step ii).

In another aspect of the invention there is provided a method, cited in claim 42, for determining the amount of fertiliser to apply to a soil, said method comprising the steps of i) determining a gross N-mineralization rate according to the method of claim 1, ii) including said gross N-mineralization rate determined in step i) in a calculation of the amount of fertiliser required to supplement said soil with an amount of nitrogen equal to the amount of nitrogen being mineralized, and iii) determining a total nitrogen demand of a crop over a period of time, and iv) applying to said soil a fertiliser containing an amount of nitrogen corresponding to the sum of a) and b), where a) is the total amount of nitrogen being mineralized over said period of time indicated in step iii), and b) is the amount of nitrogen corresponding to the difference between said total nitrogen demand determined in step iii) and a), with the proviso that the total nitrogen demand determined in step iii) exceeds a), and with the further proviso that no fertiliser is added, when the total nitrogen demand determined in step iii) does not exceed a).

In another aspect of the invention there is provided a method, cited in claim 43, for determining the amount of fertiliser to apply to a soil, said method comprising the steps of i) determining a gross N-mineralization rate according to the method of claim 25, ii) including said gross N-mineralization rate determined in step i) in a calculation of the amount of fertiliser required to supplement said soil with an amount of nitrogen equal to the amount of nitrogen being mineralized, and iii) determining a total nitrogen demand of a crop over a period of time, and iv) applying to said soil a fertiliser containing an amount of nitrogen corresponding to the sum of a) and b), where a) is the total amount of nitrogen being mineralized over said period of time indicated in step iii), and b) is the amount of nitrogen corresponding to the difference between said total nitrogen demand determined in step iii) and a), with the proviso that the total nitrogen demand determined in step iii) exceeds a), and with the further proviso that no fertiliser is added, when the total nitrogen demand determined in step iii) does not exceed a).

In yet another aspect there is provided a method, cited in claim 44, for determining the amount of fertiliser to apply to a soil, said method comprising the steps of i) determining the gross N-mineralization rate according to the method of claim 35, ii) including the gross N-mineralization rate determined in step i) in a calculation of the amount of fertiliser required to supplement the soil with an amount of nitrogen equal to the amount of nitrogen being mineralized, and iii) determining a total nitrogen demand of a crop over a period of time, and iv) applying to the soil a fertiliser containing an amount of nitrogen corresponding to the sum of a) and b), where a) is the total amount of nitrogen being mineralized over the period of time indicated in step iii), and b) is the amount of nitrogen corresponding to the difference between the total nitrogen demand determined in step iii) and a), with the proviso that the total nitrogen demand determined in step iii) exceeds a), and with the further proviso that no fertiliser is added, when the total nitrogen demand determined in step iii) does not exceed a).

A number of practical applications of the present invention are listed below. These applications are described in order to demonstrate the wide range of applicability of the present invention.

The productivity of an agricultural soil is mainly governed by two key parameters, namely the water holding capacity of the soil and the potential for supplying the crops with nutrients (and water) during the growing season. The two parameters depend on topography, geology, soil texture, cropping and management history and are to some extent correlated. Clay soils for example have high water holding capacities and often also high contents of organic nitrogen and N-mineralization rates. The optimum nitrogen-application rate varies considerably among fields and within fields. Under Danish conditions is has been found that the optimum nitrogen-application rates within one field varied between 0 and 150 kg nitrogen per hectare with an optimum around 125 kg nitrogen per hectare on approximately half of the field (Simmelsgaard and Andersen, 1995).

In order to take into account the within field variation, a programmed and differentiated fertilisation plan must be based on soil maps for pedocells of perhaps 20×20 m showing plant available soil moisture, inorganic plant nutrients and the potential for nitrogen-supply of the soil, i.e., the nitrogen-mineralization determined according to the present invention.

Soil maps may be constructed from intensive soil sampling and soil analyses or a combination of soil sampling and yield mapping. Yield mapping is more or less a standard equipment on e.g. Massey Ferguson harvesters and gives a readily available first mapping of the fields based on which detailed analyses can be designed. Furthermore, nitrogen-fertiliser demand and crop nitrogen-demand can be regarded as synonyms for the additional nitrogen fertiliser requirement of a certain crop on a particular field, and the present invention can thus also be employed as a method for assessing crop nitrogen-demand.

Following estimation of the gross rate of N-mineralization at a particular square grid position of a field at a particular point in time according to the methods of the present invention, this rate is then convertible to the total amount of inorganic nitrogen generated in a particular acreage over a given period of time. The farmer thus receives valuable information on the inherent capacity of a particular subsection of the soil to supply nitrogen to the crops over a predetermined period of time. The acreage of the subsection in question and the period of time included in the estimation may vary according to e.g. soil conditions and variations herein including pore size and water content, changing climatic conditions affecting the rate of gross N-mineralization, crop growth and subsequently crop nitrogen demand. However, as exemplified herein below, the present method also facilitates correlating arginase activity with gross N-mineralization rates during a growth season, i.e. a period of time wherein changing and dynamic conditions mediates seasonal variations of gross N-mineralization and arginase content in the same soil subsection.

"Within field" soil analyses of N-mineralization rates is one prominent application of the present invention. It is made possible by the ease by which the analysis can be performed and the low costs associated with the analysis. It is furthermore well suited to be adapted to mobile units for on-line soil analyses which is the most resent trend in soil sampling. The positioning systems are developed as well as the fertiliser sprayers able to adjust application rates continuously such as the GPS assisted KEMISTAR fertiliser spreader system by KEMIRA.

"Among field" soil analyses is also a prominent application of the invention. N-mineralization is dependent on cropping and management history of whole fields which is usually not recorded. Years of animal manure application is well known to increase the N-mineralization of soils and there is a special need to be able to detect those soils which for cropping and management reasons may have increased N-mineralization. Any farmer or adviser may thus design a simple sampling strategy in accordance with the present invention in order to detect the N-mineralization in a number of fields and thus adjust fertilisation accordingly. Because manure has been applied—and still is being applied—to a large fraction of Danish fields, a closer detection of the fields with a history of many years manure application and quantification of N-mineralization may have a significant effect on the use of fertilisers in Denmark and thus the nutrient losses to the environment.

Inorganic soil nitrogen may also be measured by use of a mineralization kit adapted to measure ammonia as well as nitrates. The invention thus opens for the complete analysis of the important crop production parameters.

Alternative applications of the invention are associated with any process industry wherein microbial cells are engaged to perform specific functions. In, e.g. sewage treatment plants it may be useful to have indications of the state of biological processes in order to adjust flow rates, total loads, temperature etc. Environmental quality assessment may also be one alternative use. In the restoration of lakes it is important to know the mineralization of sediments in order to design the more optimal strategy. Bioremediation of polluted soils, i.e. the process of e.g. regenerating a natural habitat, is another area of application. The invention may also be employed to asses the extent to which polluted soils are being affected by the pollution.

Accordingly, in one embodiment, the method for determining the amount of fertiliser to apply to a soil is used in performing an on-line soil analysis. This analysis has the objective of providing direct information on the amount of fertiliser needed, if any. In a preferred embodiment, the method is used in connection with a precision farming system. In a particularly preferred embodiment, the method for determining the amount of fertiliser to apply to a soil is used with a mobile unit fitted with global positioning system (GPS). The method may e.g. be used in determining the coordinates of a global positioning system (GPS).

In another preferred embodiment the method is used in determining the gross N-mineralization of individual soil maps of pedocells. There is also provided a method for use in yield mapping.

In yet another embodiment, there is provided a method for determining a gross rate of N-mineralization in an agricultural field of crops by means of a series of static determinations, i.e. determinations of a gross N-mineralization rate at a particular position at a particular time. In another embodiment, there is provided the possibility of performing a series of dynamic determinations, i.e. determinations of a gross rate of N-mineralization in a particular position over time such as e.g. throughout a growth season.

In a further embodiment, there is provided a method for tracking a "management history" of a field. There is also provided a method for determining nitrate and ammonia in e.g. ecologically sensitive areas such as e.g. marshes, wetlands, lakes, and rivers. The method can be used for assessing the restoration of such sensitive areas.

In a further aspect there is provided a test-kit for use in determining the gross N-mineralization rate of a soil.

In an even further aspect there is provided a test-kit for use in determining the amount of fertiliser to apply to a soil.

In a yet further aspect there is provided a test-kit for use in correlating a correlatable urea turn-over rate of a soil with the gross N-mineralization rate of said soil.

Test-kits according to the present invention are characterised by comprising a carrier of information facilitating e.g. correlating the activity of a microbial enzyme of a functional ornithine acid cycle contained in a soil sample with the corresponding gross N-mineralization rate of said sample.

More particularly, there is provided a test-kit for use in determining the gross N-mineralization rate of a soil sample, said test-kit comprising a) a carrier of information showing corresponding values of microbial enzyme activities of a functional ornithine acid cycle and gross N-mineralization rates and b) means for determining the microbial enzyme activity of a functional ornithine acid cycle in said soil sample. In preferred embodiments, the microbial enzyme activity is the activity of an enzyme of an arginine-urea pathway such as e.g. arginine deaminase (arginase). In another preferred embodiment, the carrier of information is in the form of a standard curve provided on a support.

The test-kits of the invention may e.g. perform a correlation of said enzyme activity contained in any soil sample with a known standard curve in order to determine the gross N-mineralization rate of said sample.

In another embodiment, the carrier of information comprises a spectroscopic indicator such as e.g. a colometric or a fluorometric indicator for indicating e.g. the activity of a microbial enzyme of a functional ornithine acid cycle present in a soil sample. A colometric indicator monitors a colometrically detectable compound resulting from the action of said enzyme. A fluorometric indicator monitors a fluorometrically detectable compound resulting from the action of said enzyme. The spectroscopic indicator may also indicate the gross N-mineralization rate of the soil sample and/or the correlation of said enzyme activity with said rate of gross N-mineraliation.

In yet another embodiment the test-kit is adaptable for adaptation to a mobile unit for on-line soil analysis. In one embodiment, the test-kit is adapted for use in a positioning system, such as e.g. a global positioning system, or in a global positioning system (GPS). In another embodiment the test-kit is adapted for use with a fertiliser sprayer adjusting fertiliser application rates continuously such as e.g. the GPS assisted KEMISTAR fertiliser spreader system manufactured by KEMIRA.

The test-kit in a yet further embodiment provides information on the gross N-mineralization rate of a soil sample and facilitates the generation of and/or use of a digital map of an agricultural field enabling the farmer to use a fertiliser spreader equipped with a global positioning system (GPS) and a personal computer (PC) in order to adjust fertiliser application in accordance with the nitrogen-content of a particular grid position and the specific crop nitrogen-demand of said grid position.

The Role of Arginase in N-mineralization

Microbial cells are able to adapt to stress conditions such as drought, adverse temperature shifts, and changing nutritional conditions including depletion of essential nutrients in the environment, by e.g. forming dormant cells, i.e. living cells with hardly any metabolic activity. The cells have retained the ability to revert to vegetative growth, if and when the essential nutrients again become bioavailable, e.g. when supplied by a farmer in the form of a fertiliser, or as a result of rewetting of the soil. Dormant cells may retain a minimal amount of measurable enzyme activity involved in specific metabolic processes, but such process rates are often so insignificant that in reality, they are very difficult, if not directly impossible, to measure.

The present invention exploits the discovery that excess nitrogen is released in the form of urea, which subsequently is converted to ammonia and carbon dioxide by the enzyme urease present in the soil. Accordingly, in view of the present invention, it is necessary to redefine the concept of gross N-mineralization. This process can now be regarded as comprising as its major, final step, an arginase mediated formation of urea and release hereof into the soil. It cannot be excluded, however, that additional, minor contributions to gross N-mineralization are made by ammonia or other inorganic or organic nitrogen-compounds originating from metabolic pathways different from the arginase-urea pathway.

Arginase (arginine deaminase) is an enzyme catalysing the conversion of arginine to ornithine under the release of urea. The arginase enzyme is an intracellular enzyme and forms part of a functional ornithine acid cycle such as e.g. the conventional urea cycle.

In the initial step of the conventional urea cycle cited in standard textbooks, carbamyl phosphate reacts with ornithine to form citruline in the presence of the enzyme ornithine transcarbamylase. The next step of the cycle is the formation of arginine from citruline. This formation is catalyzed by two enzymes. The first of these, argininosuccinic synthetase, catalyzes the formation of argininosuccinic acid from citruline and aspartic acid. The subsequent cleavage of argininosuccinic acid is catalyzed by the arginino-succinic cleavage enzyme and results in the generation of arginine and fumaric acid. Thus, ornithine transcarbamylase, argininosuccinic synthetase, and argininosuccinic cleavage enzyme mediate the formation of arginine, which is subsequently hydrolysed irreversibly by means of the deamination catalysed by arginine deaminase (arginase). The irreversible deamination of arginine leads to the formation of ornithine and urea, and ornithine is thus regenerated and may reenter the conventional urea cycle in the above-described ornithine transcarbamylase-mediated reaction. Accordingly, the above cyclical events lead to the formation of urea based on ammonia, carbon dioxide and an amino group donated by aspartic acid. Importantly, however, it is the arginase activity which makes urea formation possible.

Arginase plays a fundamental role in N-mineralization, as all nitrogen originating from organic material must pass through a functional ornithine acid cycle such as e.g. the conventional urea cycle and subsequently through the arginine-urea pathway.

The arginase enzyme can be assayed with ease and was surprisingly found to be expressed by microorganisms in a soil at a level directly proportional to the rate of N-mineralization of the same soil. The degree of correlation of arginase activity with N-mineralization was established by comparing the results generated by an assay of arginase activity with the results of an isotope dilution technique exploited in order to measure directly the process of N-mineralization. The correlation enables determination of the N-mineralization rate and the corresponding crop nitrogen demand by measuring the activity of the arginase enzyme in a soil sample.

In summary, the invention can be regarded as being based on three assumptions:

That gross N-mineralization is to be taken as an index of soil fertility and thus fertiliser or crop nitrogen demand, that arginase activity is an index of gross N-mineralization, and that substantially all of the nitrogen of organic nitrogen-containing compounds passes the arginine-urea pathway, when being mineralized.

An agricultural soil may contain up to as many as 10.000 microbial species per gram. Accordingly, many different metabolic pathways for the degradation of organic compounds exist and much research has been focused on enzymes produced by soil microorganisms in order to attempt to correlate an enzymatic activity with a specific microbial parameter and/or process rate.

It is relevant to consider the fact that N-mineralization mediating microbial exoenzymes in soils are often released into a harsh and reactive environment. The exoenzymes may be hydrolysed by proteases or, alternatively, they may interact with clay minerals and be adsorbed onto a clay-mineral complex, while essentially maintaining their catalytic activity. Absorption may also, to a certain extent, protect the enzymes from decay and it has been speculated that such physical protection of exoenzymes in soil may play a special role in decomposition reactions. Free exoenzymes are thus present in the soil solution for a short time while adsorbed or protected exoenzymes may retain their activity for a considerably longer period of time, i.e., months or perhaps even years.

For the purpose of the present application, it is important to stress that exoenzymes maintain their catalytic properties when fixed in the soil matrix. Thus, assays of exoenzymes such as proteases cannot reflect the dynamic properties of N-mineralization in soil. The concept of stable enzyme components in soil has been reviewed by Burton and McGill (1989). Contrary hereto, cell-bound enzymes including intracellular enzymes, are not in contact with soil minerals and thus readily induced or repressed as a function of the presence and/or amount of a substrate and/or a product, respectively. An assay of an intracellular enzyme is therefore particularly preferred for generating a reliable index of microbiologically mediated processes such as N-mineralization.

In the context of the present invention, it is assumed that enzymes other than arginase may be employed as more or less suitable indices of N-mineralization. Such enzymes may be those involved in a functional ornithine acid cycle such as e.g. a conventional urea cycle, i.e. enzymes such as e.g. ornithine transcarbamylase, argininosuccinic synthetase, and argininosuccinic cleavage enzyme.

Arginase kinetics and the Michaelis-Menten Equation.

An enzymatically catalyzed reaction, such as the arginine deaminase (arginase) catalysed conversion of arginine to ornithine and urea, consists of three steps: (1) formation of an enzyme-substrate complex, (2) catalysis, i.e. converting substrate to product, and (3) release of product. Catalysis is often very rapid compared to the other two events; hence, either binding or release becomes the "rate-limiting" step in the reaction.

A simple equation, the so-called Michaelis-Menten equation, can be derived and describes the rate at which a given substrate is utilized (i.e., the velocity, v, of the reaction) in terms of readily measured variables. The Michaelis-Menten equation predicts that $$v = V_{max}/(1 + K_m/[S])$$

Here $V_{max}$ represents the maximum velocity of the reaction, or the maximum number of substrate molecules that a single enzyme can convert to product in a unit of time. That maximum is attained only at an infinite concentration of substrate because only then will the enzyme always be saturated with substrate. [S] is the substrate concentration and $K_m$ represents the Michaelis Menten constant. It is equivalent to the concentration of substrate needed to achieve half of the maximum velocity, i.e. $v = \frac{1}{2} V_{max}$.

The Michaelis-Menten equation is derived from the following assumptions and is therefore limited in its applicability to conditions where these assumptions are valid: (1) catalysis is rapid relative to the rates of binding and release; (2) for every molecule of substrate bound to the enzyme, a molecule of product is immediately released (the so-called steady state hypothesis); and (3) the rate at which product is bound back to the enzyme in a putative reverse reaction is negligible. The first assumption, as explained earlier, is generally valid for enzymes and the second assumption, i.e. steady state, is usually reached within milliseconds of initiating a reaction.

With respect to the third assumption, the absence of a reverse reaction, can be assured experimentally by starting with zero concentration of product and terminating the period of observation before any significant concentration of products appears. Also, since a collision between enzyme and product is a necessary prerequisite to the reformation of an enzyme-product complex, keeping the product concentration low minimizes the number of collisions and hence the rate of reverse reaction. Of cause, when the catalysis is irreversible, such as the arginine deaminase catalysed deamination of arginine, no reverse reaction takes place.

The two constants, $V_{max}$ and $K_m$, do not completely describe an enzymatically catalyzed reaction; as they by themselves predict neither the equilibrium nor the standard free energy change for a reaction. Nevertheless, they are extremely valuable. Since the conditions for which the Michaelis-Menten equation is valid are easily attained in vitro, and often approximated in vivo, $V_{max}$ and $K_m$ permit prediction of the velocity of a reaction for a given availability of substrate.

The equation $$(1/v) = (K_m/V_{max}) \times (1/[S]) + (1/V_{max})$$

is directly derivable from the Michaelis-Menten equation and is termed a Lineweaver-Burk plot. The plot predicts that a plot of $1/v$ vs. $1/[S]$ generates a straight line with a slope of $K_m/V_{max}$ and an intercept on the $1/v$ axis of $1/V_{max}$. In addition, the extrapolated intercept on the independent (substrate) axis will have a value equal to $-1/K_m$. In this way, both the Michaelis-Menten constant and the maximum velocity may be obtained from a relatively small number of observations made under conditions where the maximum velocity is not closely approached. Alternatively, the determination of $K_m$ and $V_{max}$ may also be done by methods exploiting non-linear regression analysis. Such methods will be known by the person skilled in the art.

As an alternative to a Lineweaver-Burk plot, the velocity itself may be plotted against [S]. Such a curve is hyperbolic, approaching $V_{max}$ gradually as [S] approaches infinity:

$$v = (V_{max} \times [S])/(K_m + [S])$$

The relationship predicted by the above-mentioned equation is indeed observed for arginase, as described in detail in Example 1, where measurements are made over a wide range of substrate concentrations, with some of the concentrations high enough to make the position of the true maximum clear. Accordingly, both $V_{max}$ and $K_m$ may be obtained and are indeed calculated in this manner in Example 1. The maximum value on the v axis is $V_{max}$, and values of $K_m$ are read from the graphs depicted in Example 1 as [S], when $v=\frac{1}{2}V_{max}$.

EXAMPLES

Example 1

Soils, Arginase Assay and Kinetics of the Arginase Enzyme

The objective of the example is to demonstrate that the arginase enzyme obeys simple Michaelis-Menten kinetics.

All soil samples analysed were collected form the experimental site Snubbekorsgard, Taastrup, Denmark, belonging to the Royal Veterinary and Agricultural University of Copenhagen. The soil is a sandy loam with 3.0% clay, 10% silt, 39.5% fme sand and 47.5% course sand.

Samples were collected in the upper 5 cm soil layer from subsections of the site with differing cropping histories. One soil had been uncropped for 3 years and is referred to as set aside soil. Other subsections were cropped with barley, winter wheat and ryegrass. Soils were sieved 2 mm to remove course plant litter and roots. This soil is referred to as bulk soil.

Rhizophere soil was sampled from the roots of barley stubbles by digging the roots with the adhering soil out of the soil. The stubbles were gently shaken by hand to remove bulk soil and subsequently shaken more vigorously to remove the adhering rhizophere soil that was collected and defined as rhizophere soil.

Arginase activity contained in the soils was assayed by using a standard method comprising the following steps:

(a) 4 replicates of 0.1 g soil samples were weighed into 1.5 ml Eppendorf tubes and amended with 0.2 ml non-buffered substrate solution of 1 mM arginine, (b) the soil slurries were whirl mixed and incubated at 20° C. for 2 hrs, (c) the incubations were stopped by addition of 0.8 ml ice cold 2 M KCL solution, (d) gently end-over-end shaken for 1 min., (e) subjected to centrifugation (15000×g) for 5 min., and (f) the supernatant was collected and frozen for subsequent analysis.

Controls (3 replicates) were prepared as described above, but the KCl solution was added immediately after substrate addition and thus not incubated.

The urea released during the assay is converted quantitatively to ammonia as described by (Nielsen et al., in press). The concentration of $NH_4^+$ ions in the KCl extracts was determined according to the method of Verdouw et al. (1977). The amount of $NH_4^+$ generated during the assay is thus an indirect determination of the assayed arginase activity. Importantly, excess arginine (1 mM) is added prior to assaying arginase activity in order to ensure steady-state kinetics and a maximum rate (i.e. $V_{max}$) of conversion of substrate to product. Accordingly, $V_{max}$ represents the maximum velocity of the reaction, or the maximum number of substrate molecules that a single enzyme can convert to product in a unit of time. In theory, that maximum is attained only at an infinite concentration of substrate because only then will the enzyme be saturated with substrate. However, the results presented in FIG. 1 and FIG. 2 clearly show that for all practical purposes, 1 mM arginine is sufficient to generate $V_{max}$ and simple Michaelis-Menten kinetics. Using 1 mM arginine ensures proportionality between enzyme activity and enzyme content.

Figure 1:
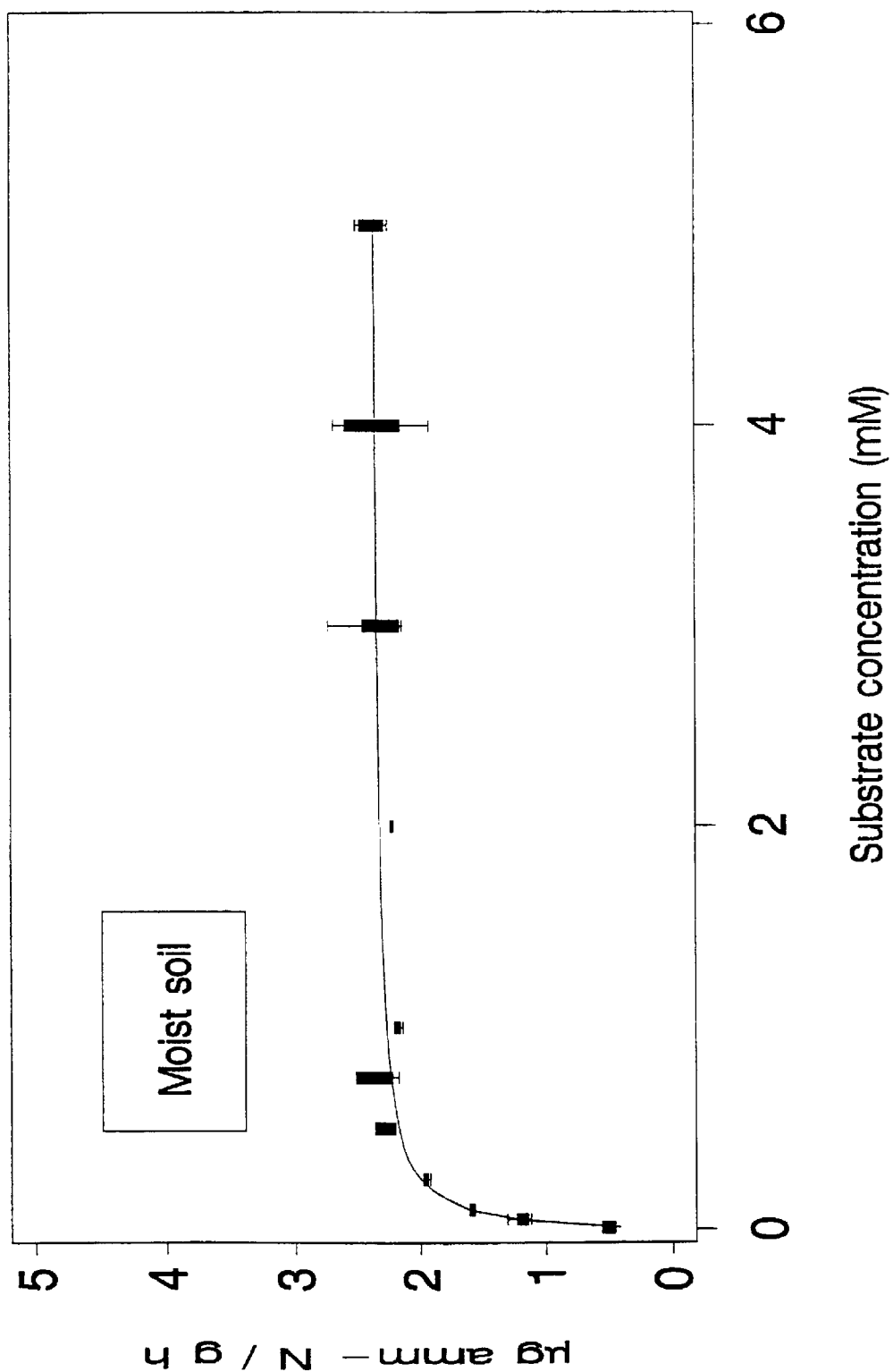
FIG. 1 illustrates the amount of ammonium generated per gram moist soil per hour [$\mu$g NH4$^+$–N/gram soil×hour] as a function of different arginine concentrations [mM]. The term "NH$_4^+$–N" designates that the rate relates to the amount of nitrogen produced. A maximum conversion of arginine to ammonium is achieved, when the concentration of arginine is 1 mM or higher. The steady-state conversion generates approximately 2.2 $\mu$g NH$_4^+$–N per gram soil each hour [2.2

FIG. 1 illustrates the amount of ammonium generated per gram moist soil per hour [μg $NH4^+$-N/gram soil×hour] as a function of different arginine concentrations [mM]. A maximum conversion of arginine to ammonium is achieved, when the concentration of arginine is 1 mM or higher. The maximum conversion generates approximately 2.2 μg $NH4^+$-N per gram soil each hour [2.2 μg $NH4^+$-N/gram soil×hour].

The arginase enzyme exhibits simple Michaelis-Menten kinetics and thus, the two parameters $V_{max}$ and $K_m$ of the Michaelis-Menten equation, describing fundamental characteristics of an enzyme, were used to characterise arginase of the arginine-urea pathway.

The equation $$v=V_{max}\times[S]/([S]+K_m)$$

represents classical Michaelis-Menten kinetics, where v is the enzyme activity (the rate at which substrate S is converted by the enzyme), $V_{max}$ is the maximal rate at which S is converted, and $K_m$ is the Michaelis-Menten constant. The maximum conversion generates approximately 2.2 μg $NH_4^+$-N per gram soil each hour [2.2 μg $NH4^+$-N 1 gram soil×hour]. As illustrated in FIG. 1, the arginase enzyme exhibits simple Michaelis-Menten kinetics and $V_{max}$ and $K_m$ were determined as 2.38 +/-0.03 [μg $NH4^+$-N/gram soil× hour] and 0.05+/-0.004 mM, respectively.

FIG. 2 illustrates the amount of ammonium generated per gram dry soil per hour [μg $NH4^+$-N 1 gram soil×hour] as a function of different arginine concentrations [mM]. A maximum conversion of arginine to ammonium is achieved, when the concentration of arginine is 0.5 mM or higher. The maximum conversion generates approximately 0.6 μg $NH4^+$-N per gram soil each hour [0.6 μg $NH4^+$-N/gram soil×hour]. The arginase enzyme exhibits simple Michaelis-Menten kinetics and $V_{max}$ and $K_m$ were determined as 0.53+/-0.02 [μg $NH4^+$-N/gram soil×hour] and 0.05 +0.01 mM, respectively. Although the dry soil reveals a considerably lower enzyme activity, simple Michaelis-Menten kinetics are still achieved.

The results illustrated in FIG. 1 and FIG. 2 strongly suggest that arginase is an intracellular enzyme because of the Michaelis-Menten kinetics, the low $K_m$ and the large decline in activity due to air drying of the soil. The kinetics for soil arginase is, to the best of our knowledge, unique, as several other enzymes studied were found to exhibit considerably more complicated kinetics and higher and/or varying $V_{max}$ and $K_m$ values.

Example 2

Formamidase Assay and Kinetics of the Formamidase Enzyme

The objective of this example is to demonstrate that arginase is a putative indicator of N-mineralization. A further objective is to illustrate desirable properties of the arginase enzyme in contrast to the properties of formamidase as an indicator of N-mineralization.

FIGS. 3–7 illustrate a comparison of the dynamics of two enzymes, arginase and formamidase, assayed under directly comparable conditions. A sample of barley soil was divided into four subsamples, A to D, and dried until the water content was approximately 5% (Day 1 of the experiment). Formamide, a substrate of formamidase, was added to subsamples A to C to final concentrations of 1 mM, 10 mM and 40 mM, respectively. Arginine was added to subsample D to a final concentration of 1 mM. All subsamples were rewetted on day 1 by adding water to a final concentration of ca. 15%

The formamidase content of the three subsamples A to C was found to be unpredictable. It thus appears that formamidase activity is not readily correlatable, or indeed correlatable in any meaningful way, with the process of N-mineralization.

In contrast to the data generated for the subsamples A to C, the data 10 generated for subsample D, the arginase assay, clearly describe all the desirable dynamics required in order to establish a correlation of arginase activity with N-mineralization. Initially, an increase in arginase activity is observed, as would have been expected following the rewetting of the sample. The arginase activity is measured by the formation of $NH_4^+$ ions [$\mu$g $NH_4^+$-N/gram soil×hour]. Once the initial "boost" of N-mineralization mediated by microbial enzymatic activities and observed immediately following rewetting has ceased, a steady state rate of N-mineralization occurs, as indicated by the essentially unchanged arginase activity assayed during days 3 to 5.

In summary, the results illustrated in FIGS. 3–7 demonstrate two important findings. Firstly, arginase activity is very responsive to the rewetting of a dry soil—exactly as would be expected for an enzyme activity indicative of the rate of gross N-mineralization. Arginase activity increases from a stable level to a level about twice the amount of activity before subsequently levelling off at the original, stable level of activity. The effect of rewetting of the soil on the arginase enzyme is important and demonstrates that arginase activity is indeed a true and dynamic indicator of in situ gross N-mineralization rates. The dynamics reflect the ability of the enzyme to indicate changing rates of N-mineralization, whereas the steady state N-mineralization observed during days 3 to 5 is characteristic of a stable rate of gross N-mineralization in soils observed at average soil water contents and temperatures during a growth season.

Secondly, formamidase activity, measured at four different substrate concentrations, responds in an unpredictable way. The response which come closest to arginase was measured at biologically excessive substrate concentrations such as substrate concentrations in excess of 50 mM formamide. Accordingly, the results cannot readily be correlated to biologically processes.

Example 3

Determination of Gross N-mineralization and Correlation With Arginase Activity

The objective of this example is to demonstrate that it is possible to correlate the arginase activity assayed in a soil sample with the rate of gross N-mineralization taking place in the same sample. Arginase activity is assayed as described in Example 1 and the rate of gross N-mineralization is determined on the basis an "isotope dilution technique" further described below.

Example 1 clearly demonstrated the applicability of the arginase enzyme in the performed assay. The present example demonstrates that arginase activity is directly correlated with the gross N-mineralization rate.

FIG. 8 illustrates a correlation of arginase activity, measured as $\mu$g $NH_4^+$-N generated per gram soil per hour, with a rate of gross N-mineralization, measured as $\mu$g nitrogen mineralized per gram soil per day. The data input represents averages of a number of paired measurements of gross N-mineralization and arginase activity on four soils collected from the experimental site over a single growing season. Of the four soils, three were cropped with barley, clover and winter wheat, respectively, while the remaining was uncropped set aside soil. It is significant that a correlation has been demonstrated for an averaged data set obtained throughout the growth season.

FIG. 8 illustrates a correlation of arginase activity with gross N-mineralization described by a Pearsson Correlation Coefficient of 0.99487 on the 99.5% level of significance.

The parameter values of the linear equation depicted in FIG. 8 are:

[Arginase activity ($\mu$g NH4$^+$-N/gram soil×hour)]=0.25+0.89× [gross N-mineralization rate ($\mu$g N/gram soil×day)]

In conclusion, the results demonstrate a direct correlation of arginase activity with gross N-mineralization rate.

The degree of correlation of arginase activity with N-mineralization was established by simply comparing the results generated by the arginase activity assay described in Example 1 with the results of a complicated and laborious isotope labelling technique previously used in measuring the process of gross N-mineralization (Blackburn, 1979).

Accordingly, all gross N-mineralization rates illustrated in FIGS. 8, 9 and 10 were determined by a modification of the $^{15}$N dilution method described by Blackburn (1979). Soils were gently mixed in a polyethylene bag and sprayed with a $^{15}$N-labelled solution of 24 mM ($^{15}NH_4)_2SO_4$ (98 atom % $^{15}$N; Cambridge isotope laboratories, Mass., USA). Spraying increased the water content by less than 2%. Subsamples of 5 grams of soil were weighed into 50 ml polyethylene centrifuge tubes with loosely attached screw caps and incubated in a water bath at a temperature of 20° C. Three replicate samples were subsampled 4 or 5 times during the incubation period. 24 ml 2 M KCl was added to each sample followed by incubation for 1 hour in an orbital shaker (1000 rpm). After centrifugation (4500×g) the supernatant was filtered through KCl-washed GF/C filters and frozen for subsequent analysis.

The $^{15}$N analysis of the $NH_4^+$ pool was conducted according to the microdiffusion assay of Risgaard-Pedersen et al. (1995) and by using a triple collector mass spectrometer (Tracermass model; Europa Scientific LTD., Crewe, United Kingdom) and manually injecting the samples.

The $^{15}$N fraction of the $NH_4^+$ pool was determined according to the method of Nielsen (1992) and the results used as input in the isotope dilution model for $NH_4^+$ turn-over (Blackburn, 1979). The method of Blackburn facilitates a determination of gross N-mineralization by measuring total $NH_4^+$ release (d) and immobilisation (i.e. assimilation of of $NH_4^+$) (i) according to two equations:

$P(t)=P(0)+(d-i)t$ $\ln[R(t)^{15}n]=\ln[R(0)-^{15}n]-[d/(d-i)]\times\ln[[(d-i)t+P(0)]/P(0)]$ where P(0) is the initial pool of $^{14}$N and $^{15}$N, P(t) is the pool of $^{14}$N and $^{15}$N at time t, $^{15}$n is the natural abundance of $^{15}$N (0.36 atom %), and R(0) and R(t) are the relative abundance of $^{15}$N (i.e. $^{15}N/(^{15}N+^{14}N)$) at times 0 and t, respectively.

When d and i are constant, P(t) is a linear function of t with a slope equal to (d−i), and $\ln[R(t)-^{15}n]$ is a linear function of $\ln[[(d-i)t+P(0)]/P(0)]$ with a slope equal to −d/(d−i) and an intercept equal to $\ln[R(0)-^{15}n]$. From linear plots generated from experimental data, the respective slopes can be calculated and used in the determination of (d) and (i).

FIG. 9 illustrates the original results used for generating the abovementioned linear equation depicted in FIG. 8. Four different types of soils were used and the rate of gross N-mineralization determined for each soil. The soils were set aside soil (circles) and soils cropped with barley (squares), clover (triangles) and winter wheat (stars), respectively. FIG. 9 illustrates that the highest rates of N-mineralization were measured for winter wheat and reflects the high nitrogen demand for this particular crop. Similarly, the set aside soil was characterized by having the lowest rate of gross N-mineralization of the four soils. The soils cropped with barley and clover were characterised by rates of gross N-mineralization being higher than the rate for the set aside soil and equal to or lower than the rate of gross N-mineralization observed for the soil cropped with winter wheat.

Averages of corresponding values of arginase activity and gross N-mineralization rates were produced for each of the four soils, and these averages were used as input data for the results illustrated in FIG. 8. The measurements of arginase activity and the calculation of gross N-mineralization rates by means of a modification of an isotope dilution technique (Blackburn, 1979) were performed during the growth season of 1995, i.e. during the months of May, June and July.

FIG. 10 illustrates the relationship between arginase activity and rate of gross N-mineralization for the entire set of data illustrated in FIG. 9. No averages were calculated. Instead, the entire set of data were pooled in order to seek a correlation based on the entire data set from each soil.

Accordingly, when the results illustrated in FIG. 9 were "pooled" (FIG. 10) the below parameter values were calculated:

[Arginase activity ($\mu$g NH4$^+$–N/gram soil×hour)] =0.45+0.68× [gross N-mineralization rate ($\mu$g N/gram soil×day)]

The correlation of arginase activity with gross N-mineralization described in FIG. 10 and by the above equation is described by a Pearsson Correlation Coefficient of 0.79133 at the 99.99% level of significance.

Example 4

Correlation of Arginase Activity With Gross N-mineralization During a Year

The objective of this example is to demonstrate that it is possible also to correlate arginase activity with gross N-mineralization throughout the growth season. The method is thus well suited for performing an analysis of the dynamic nature of the process of gross N-mineralization during a season of crop growth.

Although Example 3 clearly demonstrated the correlation of arginase activity with the rate of gross N-mineralization, a more significant documentation of the correlation of arginase activity with gross N-mineralization is the parallel, seasonal variation of the gross N-mineralization rate and arginase activity observed in the same soil. This correlation is illustrated in FIGS. 11 and 12.

FIG. 11 illustrates the seasonal variations of arginase activity ($\mu$g NH4$^+$–N/gram soil×hour) observed in bulk soil and rhizophere barley soil throughout a growth season. Day 1 is Jan. 1, 1995.

FIG. 12 illustrates the seasonal variations of the gross N-mineralization rates ($\mu$g nitrogen/gram soil×day) observed in bulk soil and rhizophere barley soil throughout a growth season. Day 1 is Jan. 1, 1995.

The results provide further evidence of arginase being an essential enzyme in the mineralization process.

Further evidence of the correlation of arginase activity with gross N-mineralization over a growth season is provided below. The data obtained at Day 240, Day 260 and Day 297 were selected in order to demonstrate a correlation under conditions characterised by significant changes in both arginase activity and gross N-mineralization rate. The correlation of arginase activity with gross N-mineralization described in FIG. 11 and FIG. 12, respectively, is described by a Pearsson Correlation Coefficient of 0.9740 at the 99.9% level of significance.

Example 5

Correlation of the Rate of Gross N-mineralization With Urea Turn-over

The objective of this example is to provide further evidence that the conversion of arginine to urea is the single most important step in determining the rate of N-mineralization in soil. The evidence presented below shows that virtually all of the mineral nitrogen generated by means of N-mineralization can be accounted for by the turn-over of urea present in the soil. Thus, the example illustrates that N-mineralization and urea turn-over are tightly correlated processes and that arginase mediated urea formation is the single most important step in measuring N-mineralization.

More particularly, the present example describes the correlation of the rate of gross $^{15}$N-mineralization, determined by the "isotope dilution technique" as described in Example 3, with the $^{14}$C-urea turn-over rate determined as described in detail below. The crux of the example is, quite simply, that the "isotope dilution technique" facilitates direct determination of the amount of $^{15}$NH$_3$ formed by means of N-mineralization, while the below-described method facilitates direct detection of 14CO$_2$ formed as a result of $^{14}$C-urea turn-over in the soil. Each mole of $^{14}$CO$_2$ formed by $^{14}$C-urea turn-over in the soil is equivalent to the formation of two moles of NH$_3$ and thus, the amount of NH$_3$ formed in this way can be directly compared to the the amount of $^{15}$NH$_3$ formed by means of N-mineralization and detected by the "isotope dilution technique". The experiment thus establishes a simple correlation between the turn-over of urea and the subsequent formation of ammonia in the soil.

The concentration of urea in soils was measured by the method of Pedersen et. al. (1995):

(a) soil samples (16 g) were weighed into 50 ml centrifuge tubes and incubated at 20° C., parallel to the incubations for $^{14}$C-urea turn-over.

(b) three replicate soil samples were extracted 3 times during the incubation period by adding 5 ml 1 M KCl containing 0.5% ZnCl$_2$ to inhibit microbial activity.

(c) after vortexing the soil, each sample was transferred into a double-chamber centrifugation unit and centrifuged (6800×g) for 10 min at 3° C.

(d) the filtrate was immediately frozen for subsequent analysis by the method of Price and Harrison (1987).

(e) absorbance was measured at 540 nm in a microplate reader (Bio Tek Instruments) and blanks were prepared for each sample by replacing the diacetylmonooxime reagent with distilled water.

The turn-over rates of $^{14}$C-urea in soil were determined by using the steady state model described by Lund and Blackburn (1989). The model is valid if the urea pool size remains constant during the incubation period and if the $^{14}$C-urea pool decreases exponentially with time. The model determines the turn-over rate constant (k) as the slope of the natural logarithm (ln) of $^{14}$C-urea content against time and the turn-over rate is determined as k multiplied with the urea pool.

The $^{14}$C-urea content (%) left in the soil during the incubation was calculated knowing the amount of added $^{14}$C-urea tracer and the amount of produced $^{14}$CO2. The turn-over rate constant was calculated from data points where less than 90% of the added $^{14}$C-urea was hydrolysed.

The $^{14}$C-urea turn-over rates in soil samples were determined in 9 ml polypropylene centrifuge tubes with a butyl stopper in the lid. Samples of 1.5 g of soil were weighed into each tube, covered with a perforated safran film, and incubated at 20° C. for approximately 15 hrs before use.

A sample of 5 $\mu$l $^{14}$C-urea solution (56 mCi/mmol $^{14}$C-urea) was added to the soil and the tube was sealed with a lid. The tubes were reincubated at 20° C. and subsampled in triplicates after 2, 4, 8, 10 and 15 min, respectively.

The urea concentration of the added tracer solution was adjusted to the indigenous urea concentration in soil, since enrichment of the natural urea pool has been shown to influence the turn-over of $^{14}$C-urea. In the standard protocol, the tracer addition increased the soil water content of the soil sample by less than 0.5%

All incubations were stopped by injecting 3 ml NaOH with a hypodermic needle through the butyl rubber stopper and violently shaking the tube. The NaOH raised the pH to approximately 14 in the soil slurry, thus terminating all microbial activity and converting the produced $^{14}$CO$_2$ gas to $^{14}$C-labelled carbonate ions. The tubes were then centrifuged (15000×g) and the supernatant frozen for subsequent analysis of the content of $^{14}$C radioactivity in the carbonate pool.

The amount of $^{14}$C trapped in the carbonate pool was determined by a microdiffusion technique. A filter paper (10 cm$^2$) was folded into a 1.5 ml centrifuge tube and 0.4 ml Carbo-sorb E (Packard) was added to the filter. The centrifuge tube was installed in a string hanging from the butyl rubber lid of a 100 ml infusion bottle. A 0.5 ml sample was placed in the infusion bottle and acidified by injecting 1.5 ml 5 N H$_2$SO$_4$ with a hypodermic needle through the lid to release CO$_2$ from the NaOH solution.

The released CO$_2$ was allowed to absorb to the Carbo-sorb overnight before the CO$_2$ trap was transferred to a 20 ml scintillation vial and filled with scintillation liquid (Ecoscient A, National Dianostics, Atlanta, Ga.). The $^{14}$C activity was measured in a Beckmann Ls 1801 scintillation counter with an automatic quench correction software programme. Radioactivity (dpm/g soil) was calculated using the soil water content and the amount of NaOH added. The $^{14}$CO$_2$ background in the $^{14}$C-urea tracer solution was subtracted from all results. The radioactivity of added tracer was determined by adding 5 $\mu$l $^{14}$C-urea tracer solution directly into the scintillation liquid.

Results are presented in Table 1 below. Three different types of soil were assayed: Set aside bulk soil, barley bulk soil and barley rhizosphere soil. Samples were collected as indicated in column 1 on Sep. 13, 1995 (A), on Oct. 23, 1995 (B), on Nov. 6, 1995 (C) and on Dec. 6, 1995 (D). Water content was determined as percentage water per dry weight (column 2). The urea pool size was determined as ng N per gram soil (column 3). The urea turn-over rate constant k and the corresponding urea turn-over rate ($\mu$g N per gram soil per day) are indicated in columns 4 and 5, respectively. The gross N-mineralization rate ($\mu$g N per gram soil per day) is listed in column 6. The assayed arginase activity is listed in column 7. N.D. indicates not determined.

The fact that the rate of urea turn-over in some cases exceed the rate of gross N-mineralization is explained by the fact that urea may be immmobilised and metabolised in the microbial cells. This is an additional fact that underlines the importance of the arginine-urea pathway.

FIG. 13 is based on the results presented in Table 1 and illustrates a correlation of the gross N-mineralization rate with the urea turn-over rate for each of the three different types of soil. The correlation of gross N-mineralization with urea turn-over rate, as depicted in FIG. 13, is described by a Pearsson Correlation Coefficient of 0.6359 at the 94% level of signifigance.

Importantly, the amount of NH$_3$ generated in the urea turn-over experiment equals the amount of NH$_3$ mineralized in the "isotope dilution technique"-experiment. Accordingly, there is a good correlation between urea turn-over and N-mineralization. This lends further support to the correlation of arginase mediated urea formation being correlated with the process of N-mineralization.

TABLE 1

Determination of urea turn-over rates, gross N-mineralization and the potential arginine ammonication rate for set aside bulk soil and barley bulk and rhizosphere soil, respectively.

| Soil sample | Water content | Urea pool size ng N/g | Turn-over rate constant k | Urea turn-over rate $\mu$g N/g d | Gross mineral rate $\mu$g N/g d | Arginase activity $\mu$g N/g h |
|---|---|---|---|---|---|---|
| Set-aside bulk | | | | | | |
| B | 9.4 ± 0.1 | 21.0 ± 5.4 | 0.110 | 3.3 ± 0.9 | 1.5 ± 0.2 | 0.5 ± 0.0 |
| C | 12.6 ± 0.0 | 17.1 ± 7.8 | 0.061 | 1.5 ± 0.7 | 0.7 | 0.5 |
| D | 12.1 ± 0.2 | 20.7 ± 8.1 | 0.051 | 1.5 ± 0.6 | 0.8 | N.D. |
| Barley bulk | | | | | | |
| A | 12.0 ± 0.0 | 20.1 ± 3.2 | 0.078 | 2.2 ± 0.4 | 2.0 | 0.7 ± 0.0 |
| B | 10.4 ± 0.1 | 16.0 ± 2.1 | 0.090 | 2.1 ± 0.3 | 1.5 ± 0.2 | 0.9 ± 0.4 |
| C | 13.0 ± 0.1 | 33.6 ± 7.5 | 0.044 | 2.2 ± 0.5 | 2.1 | 1.0 |
| Barley rhizosphere | | | | | | |
| A | 13.1 ± 0.1 | 35.7 ± 3.5 | 0.082 | 4.2 ± 0.8 | 4.0 | 1.5 ± 0.0 |
| B | 13.0 ± 0.1 | 25.0 ± 8.0 | 0.082 | 2.9 ± 0.9 | 4.8 ± 0.6 | 1.6 ± 0.1 |
| C | 13.7 ± 0.1 | 31.5 ± 7.6 | 0.035 | 1.6 ± 0.4 | 2.6 | 1.6 |

FIG. 15 is also based on the results presented in Table 1 and illustrates a correlation of arginase activity with gross N-mineralization rate for each of the three different types of soil listed in Table 1. The correlation illustrated in FIG. 15 is described by a Pearsson Correlation Coefficient of 0.85577 at the 99.4% level of significance. The results lend further support to the correlation of arginase activity with gross N-mineralization disclosed in the previous examples of this application.

As previously mentioned, a number of alternative pathways for nitrogen ,æmetabolism may be present in soil. In the rhizosphere soil, which is a small specialised environment dominated by bacteria and protozoa, it was found that on average 75% of the gross N-mineralization was explained by the arginine-urea pathway. Accordingly, this does leave space for alternative pathways of nitrogen metabolism in soil.

LITERATURE REFERENCES

Blackburn, T. H. (1979). Method for Measuring rates of NH$_4^+$ turn-over in anoxic marine sediments, using a $^{15}$NH$_4^+$-dilution technique. Appl. and Environ. Microbiol. 37, 760–765.

Burton, D. L. and W. B. McGill (1989). Role of enzyme stability in controlling histidine deaminating activity in soil. Soil Biol. and Biochem. 21, 903–910.

Burton, D. L. and W. B. McGill (1992). Spatial and temporal fluctuation in biomass, nitrogen mineralizing reactions and mineral nitrogen in a soil cropped to barley. Can. J. Soil Sci. 72, 31–42.

Lund, B. Aa. and T. H. Blackburn (1989). Urea turn-over in a coastal marine sediment measured by a 14C-urea short term incubation. J. of Microbiol. Meth. 9, 297–308.

Nielsen, L. P. (1992). Denitrification in sediment determined from isotope pairing. FEMS Microbiol. Ecol. 86, 357–362. Pedersen, H., Lomstein, B. Aa. and T. H. Blackburn (1993). Evidence for bacterial urea production in marine sediments. FEMS Microbiol. Ecol. 12, 51–59.

Price, N. M. and P. J. Harrison (1987). Comparison of methods for the analysis of dissolved urea in seawater. Marine Biol. 94, 307–317.

Risgaard-Pedersen, N., Rysgaard, S. and N. P. Revsbech (1995). Combined microdiffusion-hypobromite oxidation method for determining nitrogen-15 isotope in ammonium. Soil Sci. Soc. of America J. 59, 1077–1080.

Simmelsgaard, S. E. and M. N. Andersen (1995). The influence of nitrogen and water availability on crop yield variation. In: Proceedings of the Seminar on Site Specific Farming (Ed.: S. E. Olesen), Koldkærgaard, Aarhus, Denmark.

Verdouw, H., Van Echteld, C. J. A. and E. M. J. Dekkers (1977). Ammonia determination based on indophenol formation with sodium salicylate. Water Res. 12, 399–402.

What is claimed is:

1. Method for determination of the gross N-mineralization rate of a first soil sample, said method comprising the steps of
   i) determining the activity of a microbial enzyme of a functional ornithine acid cycle contained in said sample,
   ii) determining
      a) the activity of said enzyme in a second soil sample, and
      b) the corresponding gross N-mineralization rate of said second soil sample, and
   iii) determining the gross N-mineralization rate of said first soil sample on the basis of the gross N-mineralization rate corresponding to said activity determined in step ii).

2. Method according to claim 1 wherein said functional ornithine acid cycle is a conventional urea cycle.

3. Method according to claim 1 wherein said enzyme is selected from the group consisting of arginine deaminase (arginase), ornithine transcarbamylase, argininosuccinic synthetase and argininosuccinic cleavage enzyme.

4. Method according to claim 3 wherein said enzyme is arginine deaminase (arginase).

5. Method according to claim 4 wherein said activity is determined by measuring an amount of ammonium ions formed over time.

6. Method according to claim 1 wherein said enzyme is mediating at least one reaction selected from the group consisting of arginine deamination and urea formation.

7. Method according to claim 6 wherein said enzyme is mediating arginine deamination.

8. Method according to claim 6 wherein said enzyme is mediating urea formation.

9. Method according to claim 1 wherein said enzyme belongs to an arginine-urea pathway.

10. Method according to claim 1 wherein said enzyme exhibits simple Michaelis-Menten kinetics.

11. Method according to claim 1 wherein said enzyme exhibits Michaelis-Menten kinetics selected from the group consisting of zero order kinetics, first order kinetics, second order kinetics and combinations thereof.

12. Method according to claim 1 wherein said enzyme exhibits Michaelis-Menten first order kinetics.

13. Method according to claim 1 wherein the enzyme has a Michaelis-Menten constant, Km, measured in mM (millimolar), of less than 1.0.

14. Method according to claim 1 wherein Vmax, the maximum velocity of the reaction catalyzed by said enzyme, measured as [μg $NH_4^+$-N/gram soil×hour], is less than 4.0.

15. Method of claim 14, wherein Vmax, the maximum velocity of the reaction catalyzed by said enzyme, measured as [μg $NH_4^+$-N/gram soil×hour], is less than 2.5.

16. Method according to claim 1 wherein said sample has a weight of less than 10 grams.

17. Method of claim 16, wherein said sample has a weight of less than 5 grams.

18. Method of claim 16, wherein said sample has a weight of less than 1 gram.

19. Method of claim 16, wherein said sample has a weight of less than 0.1 gram.

20. Method according to claim 1 wherein said sample is selected from the group consisting of bulk soil, rhizosphere soil and combinations thereof.

21. Method according to claim 1 wherein a duration of said assay is less than 4 hours.

22. Method of claim 21, wherein a duration of said assay is less than 1 hour.

23. Method of claim 21, wherein a duration of said assay is less than 0.25 hour.

24. Method of claim 21, wherein a duration of said assay is less than 0.1 hour.

25. Method according to claim 1 wherein said rate is determined by $^5NH_4^+$-dilution.

26. Method according to claim 1 wherein a correlation of said activity with said rate may be determined and is characterized by a Pearsson Correlation Coefficient, said Pearsson Correlation Coefficient being at least 0.75.

27. Method of claim 26, wherein said correlation of said activity with said rate is characterized by a Pearsson Correlation Coefficient said Pearsson correlation Coefficient being at least 0.9949.

28. Method according to claim 1 wherein the correlatable relationship between said activity and said rate is expressed by a linear equation.

29. Method according to claim 28 wherein said equation is a substantially linear equation.

30. Method according to claim 30 wherein said equation is a non-linear equation.

31. Method according to claim 30 wherein said equation is substantially without any local minima and/or local maxima.

32. Method for fertilizing a soil, said method comprising the steps of
   i) determining a gross N-mineralization rate according to method of claim 1,
   ii) determining the amount of fertilizer to apply to a soil by means of a calculation which considers said gross N-mineralization rate determined in step i) and calculates the amount of fertilizer required to supplement said soil with an amount of nitrogen equal to the amount of nitrogen being mineralized, and
   iii) applying to said soil said amount of fertilizer calculated in step ii).

33. In a method of yield mapping, the improvement comprising determining the amount of fertilizer to apply to a soil by the method of claim 32.

34. In a method of biomediation the improvement comprising determining the amount of fertilizer to apply to a soil by the method of claim 32.

35. Method for fertilizing a soil, said method comprising the steps of
  i) determining a gross N-mineralization rate according to the method of claim 1,
  ii) determining the amount of fertilizer to apply to a soil by means of a calculation which considers said gross N-mineralization rate determined in step i) and calculates the amount of fertilizer required to supplement said soil with an amount of nitrogen equal to the amount of nitrogen being mineralized,
  iii) determining a total nitrogen demand of a crop over a period of time, and
  iv) applying to said soil a fertilizer containing an amount of nitrogen corresponding to the sum of a) and b) where
    a) is the total amount of nitrogen being mineralized over said period of time indicated in step iii), and
    b) is the amount of nitrogen corresponding to the difference between said total nitrogen demand determined in step iii) and a),
with the proviso that the total nitrogen demand determined in step iii) exceeds a), and with the further proviso that no fertilizer is added, when the total nitrogen demand determined in step iii) does not exceed a).

36. In a method of determining the gross N-mineralization in individual soil maps of pedocells, the improvement comprising making such determinations by the method of claim 1.

37. Method for determining the gross N-mineralization rate of a soil sample, said method comprising the steps of
  i) determining the activity of a microbial enzyme of a functional ornithine acid cycle contained in said sample,
  ii) determining said gross N-mineralization rate of said soil sample by correlating said activity determined in step i) with said rate of gross N-mineralization on the basis of
    a) determining an activity of said enzyme contained in said sample,
    b) determining a rate of gross N-mineralization of said sample,
    c) generating corresponding values of said activity determined in step a) and said rate determined in step b), said corresponding values forming a correlatable relationship between said activity and said rate, and
    d) generating a correlation of said activity with said rate based on said corresponding values generated in step c).

38. Method for fertilizing a soil, said method comprising the steps of
  i) determining a gross N-mineralization rate according to the method of claim 37,
  ii) determining the amount of fertilizer to apply to a soil by means of a calculation which considers said gross N-mineralization rate determined in step i) and calculates the amount of fertilizer required to supplement said soil with an amount of nitrogen equal to the amount of nitrogen being mineralized, and
  iii) applying to said soil said amount of fertilizer calculated in step ii).

39. Method for fertilizing a soil, said method comprising the steps of
  i) determining a gross N-mineralization rate according to the method of claim 37,
  ii) determining the amount of fertilizer to apply to a soil by means of a calculation which considers said gross N-mineralization rate determined in step i) and calculates the amount of fertilizer required to supplement said soil with an amount of nitrogen equal to the amount of nitrogen being mineralized, and
  iii) determining a total nitrogen demand of a crop over a period of time, and
  iv) applying to said soil a fertilizer containing an amount of nitrogen corresponding to the sum of a) and b), where
    a) is the total amount of nitrogen being mineralized over said period of time indicated in step iii), and
    b) is the amount of nitrogen corresponding to the difference between total nitrogen demand determined in step iii) and a),
with the proviso that the total nitrogen demand determined in step iii) exceeds a), and with the further proviso that no fertilizer is added, when the total nitrogen demand determined in step iii) does not exceed a).

40. In a method of performing an on-line soil analysis the improvement comprising determining the amount of fertilizer to apply to a soil by the method of any one of claims 32, 38, 35 or 39.

41. In a method of precision farming the improvement comprising determining the amount of fertilizer to apply to a soil by the method of any one of claims 32, 38, 35 or 39.

42. The method of any one of claims 32, 38, 35 or 39 where said amount of fertilizer is correlated, for a plurality of soil locations, with the coordinates of said locations determined according to a global positioning system (GPS).

43. The method of claim 42 where the coordinates are determined by a mobile unit fitted with GPS.

44. Method of any one of claims 32, 38, 35 or 39 where said amount is correlated, for a plurality of soil locations, with the spatial coordinates of each location.

45. Method of correlating the turn-over rate of urea to ammonium with the gross N-mineralization rate of a soil sample, said method comprising the steps of
  i) determining a urea turn-over rate of said sample,
  ii) determining a gross N-mineralization rate of said sample,
  iii) generating corresponding values of said urea turn-over rate determined in step i) and said gross N-mineralization rate determined in step ii), said corresponding values forming a correlatable relationship between said urea turn-over rate and said gross N-mineralization rate, and
  iv) establishing a correlation of said urea turn-over rate with said gross N-mineralization rate based on said corresponding values generated in step iii).

46. Method according to claim 45 wherein said urea turn-over rate is determined by determining 14C-urea turn-over.

47. Method according to claim 45 wherein said sample has a weight of less than 10 grams.

48. Method of claim 47, wherein said sample has a weight of less than 5 grams.

49. Method of claim 47, wherein said sample has a weight of less than 1 gram.

50. Method of claim 47, wherein said sample has a weight of less than 0.1 gram.

51. Method according to claim 45 wherein said sample is selected from the group consisting of bulk soil, rhizosphere soil and combinations thereof.

52. Method according to claim 45 wherein said correlation of said urea turn-over rate with said gross N-mineralization rate is characterized by a Pearsson Correlation Coefficient and a corresponding level of significance, said level of significance being at least 98%, and said Pearsson Correlation Coefficient being at least 0.79.

53. Method according to claim 45 wherein the correlatable relationship between said urea turn-over rate and said gross N-mineralization rate is expressed by an equation.

54. Method according to claim 53 wherein the equation is substantially linear equation.

55. Method according to claim 53 wherein the equation is a non-linear equation.

56. Method according to claim wherein said equation is substantially without any local minima and/or local maxima.

57. A method for the determination of the gross N-mineralization rate of a soil sample, said method comprising the steps of
   i) determining the rate of turnover of urea to ammonium in said sample, and
   ii) correlating the N-mineralization rate of said sample to said turnover rate of said sample based on the correlation established, for another soil sample, by the method of claim 45.

58. Test-kit for use in determining the gross N-mineralization rate of a soil sample, said test-kit comprising a) a carrier of information showing corresponding values of microbial enzyme activities of a functional ornithine acid cycle and gross N-mineralization rates and b) means for determining the microbial enzyme activity of a functional ornithine acid cycle in said soil sample.

59. Test-kit according to claim 58 wherein said activity is the activity of an enzyme of an arginine-urea pathway.

60. Test-kit according to claim 59 wherein the activity is that of arginine deaminase (arginase).

61. Test-kit according to claim 58 wherein said carrier of information is in the form of a standard curve provided on a support.

62. Test-kit according to claim 58 wherein said carrier of information comprises a spectroscopic indicator being selected from the group consisting of a colometric indicator and a fluorometric indicator.

63. Test-kit according to claim 58, said kit being adaptable for adaptation to a fertilizer sprayer adjusting fertilizer application rates continuously.

64. A system for adjusting fertilizer application in accordance with the nitrogen-content of a particular grid position and the specific crop nitrogen-demand of said grid position as determined by a GPS, said system comprising
   (1) a fertilizer spreader equipped with a global positioning system (GPS) and a personal computer (PC); and
   (2) a test kit according to claim 58.

* * * * *